(12) United States Patent
Kauker et al.

(10) Patent No.: US 6,342,061 B1
(45) Date of Patent: Jan. 29, 2002

(54) SURGICAL TOOL WITH INTEGRATED CHANNEL FOR IRRIGATION

(76) Inventors: Barry J. Kauker, 3500 Via Flores, Soquel, CA (US) 95073; Juan I. Perez, 3510 Moorpark Ave. Apt. 200A, San Jose, CA (US) 95117; Joseph J. Kablik, 9 Old Stonehill Rd., Tyngsboro, MA (US) 01879

(*) Notice: Subject to any disclaimer, the term of this patent is extended or adjusted under 35 U.S.C. 154(b) by 0 days.

(21) Appl. No.: 09/428,144

(22) Filed: Oct. 27, 1999

Related U.S. Application Data

(60) Continuation-in-part of application No. 09/318,299, filed on May 25, 1999, which is a continuation of application No. 09/093,484, filed on Jun. 8, 1998, now Pat. No. 5,928,257, which is a division of application No. 08/713,434, filed on Sep. 13, 1996, now Pat. No. 5,792,167.

(51) Int. Cl.[7] .............................................. A61B 17/14
(52) U.S. Cl. ...................................................... 606/180
(58) Field of Search ................................ 606/180, 170, 606/167, 171, 159; 604/22, 34, 35

(56) References Cited

U.S. PATENT DOCUMENTS

| 3,568,318 | A | 3/1971  | Martin         |
|-----------|---|---------|----------------|
| 3,618,611 | A | 11/1971 | Urban          |
| 3,623,474 | A | 11/1971 | Heilman et al. |
| 3,674,024 | A | 7/1972  | Cirillo        |
| 3,678,934 | A | 7/1972  | Warfield et al.|

(List continued on next page.)

FOREIGN PATENT DOCUMENTS

| CA | 1 130 163   | 2/1979 |
| CA | 1 145 636   | 5/1983 |
| CH | 635 9099 A5 | 5/1993 |
| DE | 28 48 314   | 5/1979 |

| DE | 30 06 577 | 9/1980 |

(List continued on next page.)

OTHER PUBLICATIONS

Dyonics Disposable Blades Are The Right Tools, P/N 1060112 Jun. 1989 (3 sheets).
Stryker MicroElectric Arthroplasty System, Maintenance Manual & Operating Instructions, 277–710–3 REV. Jun. 1985 (4 sheets).
3M Arthroscopy Pump, 70–2008–1302–3 (39.75) TP (6 sheets).
Stryker The Complete Powered System for Arthroscopic Joint Surgery (3 sheets).
Stryker Intra–Articular Debrider, 5088801S10 (4 sheets).
Smith+Nephew Dyonics, Extending Your Arthroscopic Reach, 292 D 1979 12.5M 1030067 (4 sheets).

(List continued on next page.)

Primary Examiner—Kevin Truong

(57) ABSTRACT

A surgical tool designed for irrigated microsurgery or pediatric surgery. The tool includes an outer hub that is fixed to a complementary handpiece. An outer tube extends forward from the outer hub. An inner hub is coupled to a drive member integral with the handpiece to rotate in unison with the drive member. An inner tube extends forward from the inner hub and is disposed inside the outer tube. A cutting member is located on the forward end of the inner tube. The inner wall of the outer tube and the adjacent outer wall of the inner tube are in close proximity to each other. Irrigation fluid is introduced between the tubes through an opening in the outer hub. The outer wall of the inner tube is formed with a flat that extends longitudinally along the tube from the section of the inner tube that is subtended by the opening for the irrigation fluid to the distal end at which the cutting assembly is located. The flat defines a channel between the tubes through which the irrigation fluid flows from the opening to the cutting assembly. A suction from the surgical site is drawn through the center of the inner tube and the inner hub.

24 Claims, 18 Drawing Sheets

U.S. PATENT DOCUMENTS

| | | |
|---|---|---|
| 3,701,345 A | 10/1972 | Heilman et al. |
| 3,732,858 A | 5/1973 | Banko |
| 3,844,272 A | 10/1974 | Banko |
| 3,882,872 A | 5/1975 | Douvas et al. |
| 3,912,168 A | 10/1975 | Mullins et al. |
| 3,937,722 A | 2/1976 | Banko |
| 3,945,375 A | 3/1976 | Banko |
| 3,960,466 A | 6/1976 | Taylor |
| 3,990,453 A | 11/1976 | Douvas et al. |
| 3,993,054 A | 11/1976 | Newman |
| 3,995,619 A | 12/1976 | Glatzer |
| 3,996,935 A | 12/1976 | Banko |
| 4,011,869 A | 3/1977 | Seiler, Jr. |
| 4,014,342 A | 3/1977 | Staub et al. |
| 4,084,588 A | 4/1978 | Koenig |
| 4,138,205 A | 2/1979 | Wallach |
| 4,167,944 A | 9/1979 | Banko |
| 4,179,249 A | 12/1979 | Guttmann |
| 4,203,444 A | 5/1980 | Bonnell et al. |
| 4,210,146 A | 7/1980 | Banko |
| 4,239,464 A | 12/1980 | Hein |
| 4,246,902 A | 1/1981 | Martinez |
| 4,267,836 A | 5/1981 | Whitney et al. |
| 4,274,414 A | 6/1981 | Johnson et al. |
| 4,276,023 A | 6/1981 | Phillips et al. |
| 4,368,734 A | 1/1983 | Banko |
| 4,512,344 A | 4/1985 | Barber |
| 4,516,571 A | 5/1985 | Buchan |
| 4,517,977 A | 5/1985 | Frost |
| 4,548,553 A | 10/1985 | Ferster |
| 4,552,516 A | 11/1985 | Stanley |
| 4,559,040 A | 12/1985 | Horres et al. |
| 4,576,211 A | 3/1986 | Valentini et al. |
| 4,598,710 A | 7/1986 | Kleinberg et al. |
| 4,599,055 A | 7/1986 | Dykstra |
| 4,601,290 A | 7/1986 | Effron et al. |
| 4,603,694 A | 8/1986 | Wheeler |
| 4,646,736 A | 3/1987 | Auth |
| 4,646,738 A | 3/1987 | Trott |
| 4,649,919 A | 3/1987 | Thimsen et al. |
| 4,678,459 A | 7/1987 | Onik et al. |
| 4,705,038 A | 11/1987 | Sjostrom et al. |
| 4,735,558 A | 4/1988 | Kienholz et al. |
| 4,735,605 A | 4/1988 | Swartz |
| 4,747,824 A | 5/1988 | Spinello |
| 4,767,289 A | 8/1988 | Parrott et al. |
| 4,811,734 A | 3/1989 | McGurk-Burleson et al. |
| 4,815,462 A | 3/1989 | Clark |
| 4,819,635 A | 4/1989 | Shapiro |
| 4,820,265 A | 4/1989 | DeSatnick et al. |
| 4,824,339 A | 4/1989 | Bainbridge et al. |
| 4,834,729 A | 5/1989 | Sjostrom |
| 4,842,578 A | 6/1989 | Johnson et al. |
| 4,904,168 A | 2/1990 | Cavoto et al. |
| 4,909,713 A | 3/1990 | Finsterwald et al. |
| 4,923,441 A | 5/1990 | Shuler |
| RE33,258 E | 7/1990 | Onik et al. |
| 4,967,940 A | 11/1990 | Blette et al. |
| 4,982,739 A | 1/1991 | Hemstreel et al. |
| 4,983,179 A | 1/1991 | Sjostrom |
| 4,986,825 A | 1/1991 | Bays et al. |
| 4,998,527 A | 3/1991 | Meyer et al. |
| 5,007,917 A | 4/1991 | Evans |
| 5,010,876 A | 4/1991 | Henley et al. |
| 5,017,059 A | 5/1991 | Davis |
| 5,041,082 A | 8/1991 | Shiber |
| 5,047,032 A | 9/1991 | Jellicoe |
| 5,061,238 A | 10/1991 | Shuler |
| 5,074,841 A | 12/1991 | Ademovic et al. |
| 5,106,364 A | 4/1992 | Hayafuji et al. |
| 5,133,729 A | 7/1992 | Sjostrom |
| 5,135,481 A | 8/1992 | Nemeh |
| 5,152,744 A | 10/1992 | Krause et al. |
| 5,160,318 A | 11/1992 | Shuler |
| 5,192,292 A | 3/1993 | Cezana et al. |
| 5,195,960 A * | 3/1993 | Hossain et al. ............... 604/34 |
| 5,217,479 A | 6/1993 | Shuler |
| 5,219,099 A | 6/1993 | Spence et al. |
| 5,230,614 A | 7/1993 | Zanger et al. |
| 5,256,041 A | 10/1993 | Tucker |
| 5,269,798 A | 12/1993 | Winkler |
| 5,285,795 A | 2/1994 | Ryan et al. |
| 5,286,253 A | 2/1994 | Fucci |
| RE34,556 E | 3/1994 | Sjostrom et al. |
| 5,295,956 A * | 3/1994 | Bales et al. ................... 604/35 |
| 5,320,635 A | 6/1994 | Smith |
| 5,322,505 A | 6/1994 | Krause et al. |
| 5,324,301 A | 6/1994 | Drucker |
| 5,366,468 A | 11/1994 | Fucci et al. |
| 5,395,317 A | 3/1995 | Kambin |
| 5,399,160 A | 3/1995 | Dunberger et al. |
| 5,403,277 A | 4/1995 | Dodge et al. |
| 5,411,514 A | 5/1995 | Fucci et al. |
| 5,417,694 A | 5/1995 | Marik et al. |
| 5,433,588 A | 7/1995 | Monk et al. |
| 5,437,630 A * | 8/1995 | Daniel et al. ............... 606/180 |
| 5,439,464 A | 8/1995 | Shapiro |
| 5,456,722 A | 10/1995 | McLeod et al. |
| 5,484,402 A | 1/1996 | Saravia et al. |
| 5,489,291 A | 2/1996 | Wiley |
| 5,529,580 A | 6/1996 | Kusunoki et al. |
| 5,540,708 A | 7/1996 | Lim et al. |
| 5,601,583 A | 2/1997 | Donahu et al. |
| 5,611,785 A | 3/1997 | Mito et al. |
| 5,665,101 A | 9/1997 | Becker et al. |
| 5,685,838 A | 11/1997 | Peters et al. |
| 5,779,675 A | 7/1998 | Reilley et al. |
| 5,792,167 A | 8/1998 | Kablik et al. |
| 5,928,257 A | 7/1999 | Kablik et al. |
| 6,007,556 A | 12/1999 | Kablik et al. |

FOREIGN PATENT DOCUMENTS

| | | |
|---|---|---|
| DE | 3828 478 A1 | 5/1989 |
| EP | 190 000 | 8/1986 |
| EP | 445 918 A1 | 9/1991 |
| EP | 481 760 A1 | 4/1992 |
| EP | 500 146 A3 | 8/1992 |
| EP | 569 875 A1 | 11/1993 |
| EP | 609 084 A2 | 8/1994 |
| EP | 613 661 A2 | 9/1994 |
| EP | 623 317 A1 | 9/1994 |
| EP | 669 105 A2 | 2/1995 |
| EP | 677 276 A1 | 10/1995 |
| FR | 2 449 440 | 9/1980 |
| GB | 2 042 902 | 2/1979 |
| GB | 2 076 068 | 11/1981 |
| GB | 2 190 145 | 3/1987 |
| JP | 3-26887 A | 2/1991 |
| WO | WO92/08416 | 5/1992 |
| WO | WO93/04634 | 3/1993 |
| WO | WO93/225560 | 11/1993 |

OTHER PUBLICATIONS

Baxter, Edwards Orthopaedics Division, We 've Expanded Our Line So you Can Reduce Yours, 143–10 90–ORTHO (2 sheets).

Stryker Endoscopy, The Elite Arthroscopy Power System (4 sheets).

Storz, Precision Arthroplasty System, SPA–1170 (4 sheets).

Stryker Endoscopy Drawing No. 105–184–432 (1 sheet).

XOMED ENT Cutter, 8 Photographs (4 pages), Dec. 1998.

* cited by examiner

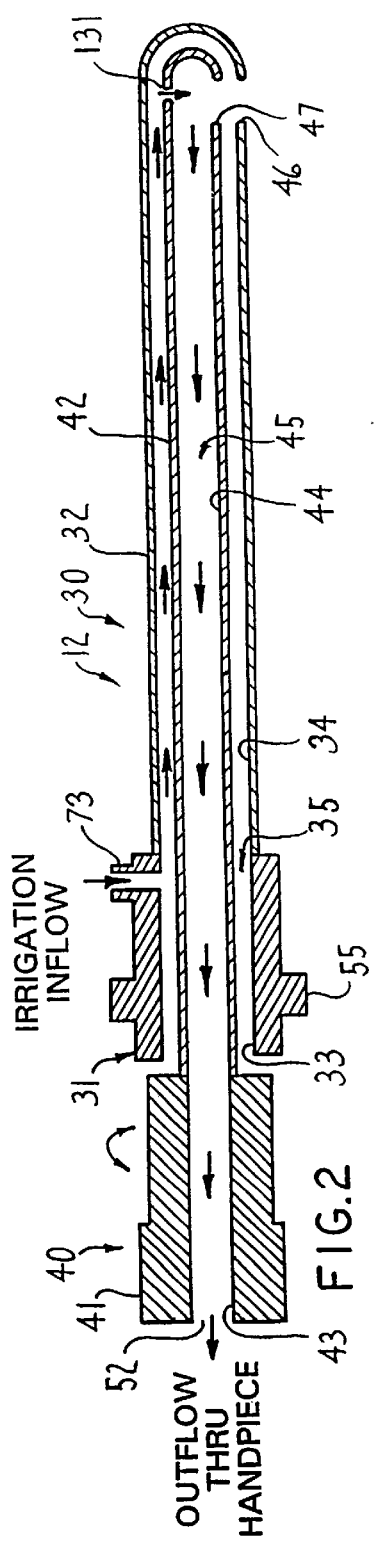
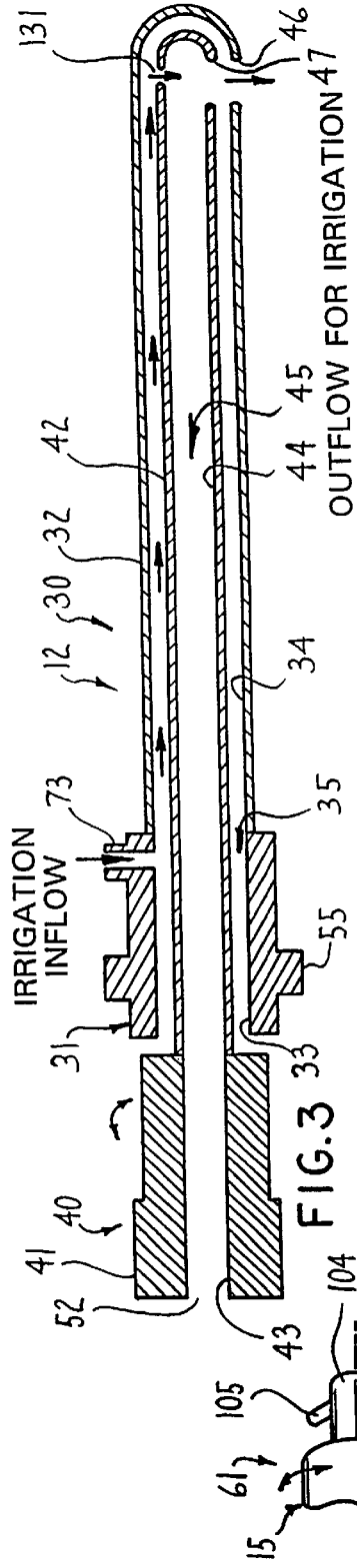
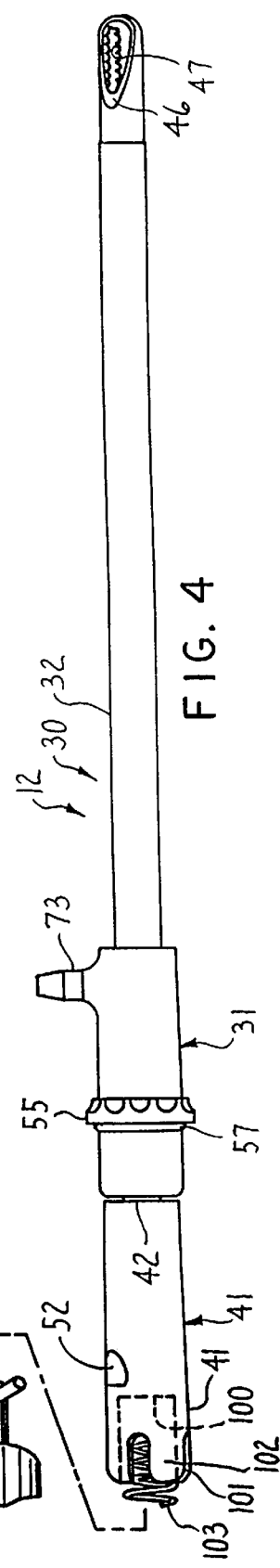

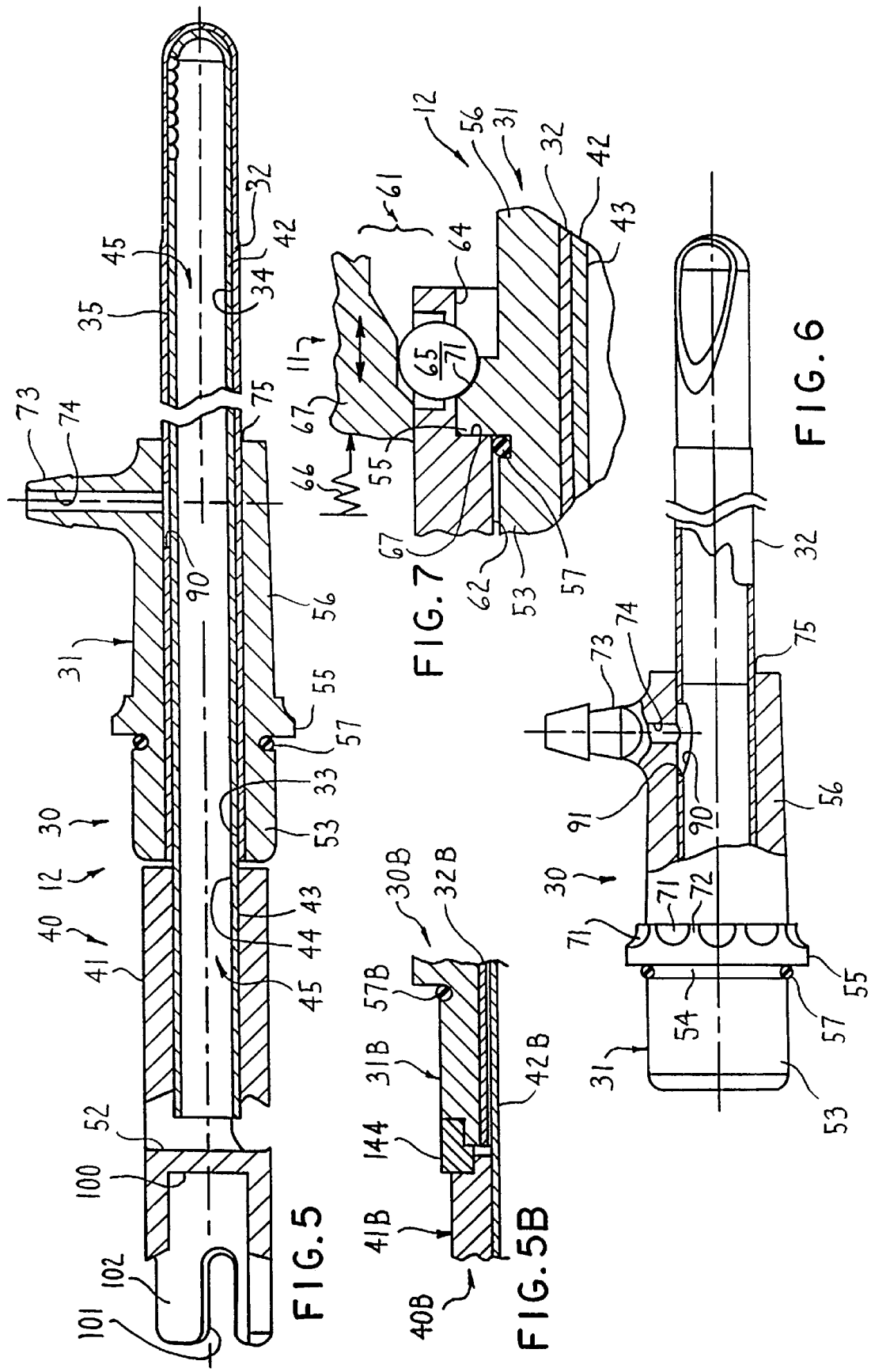

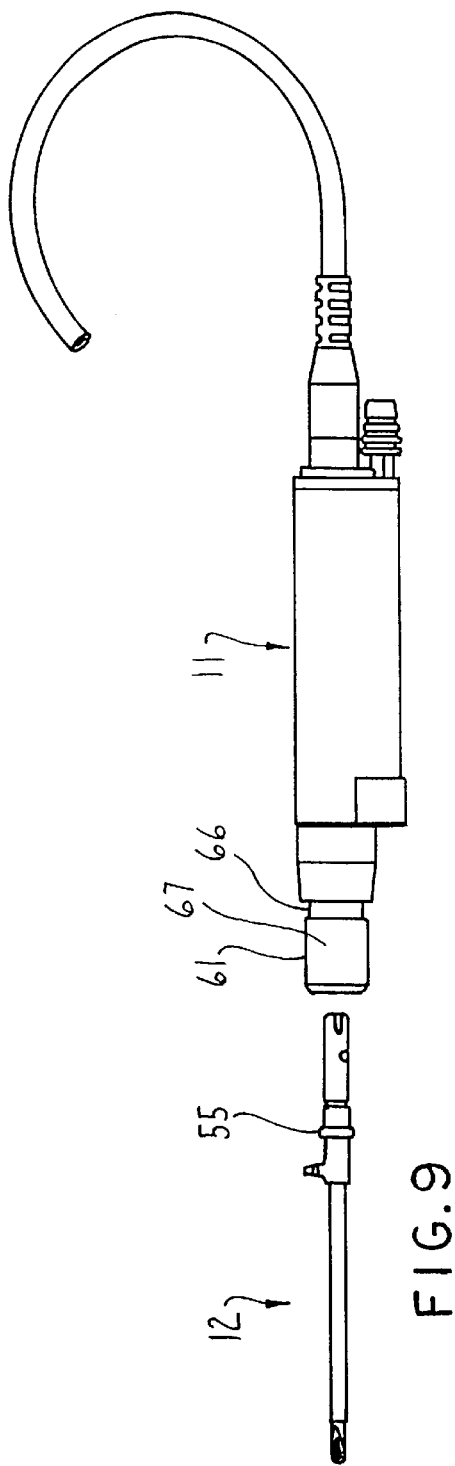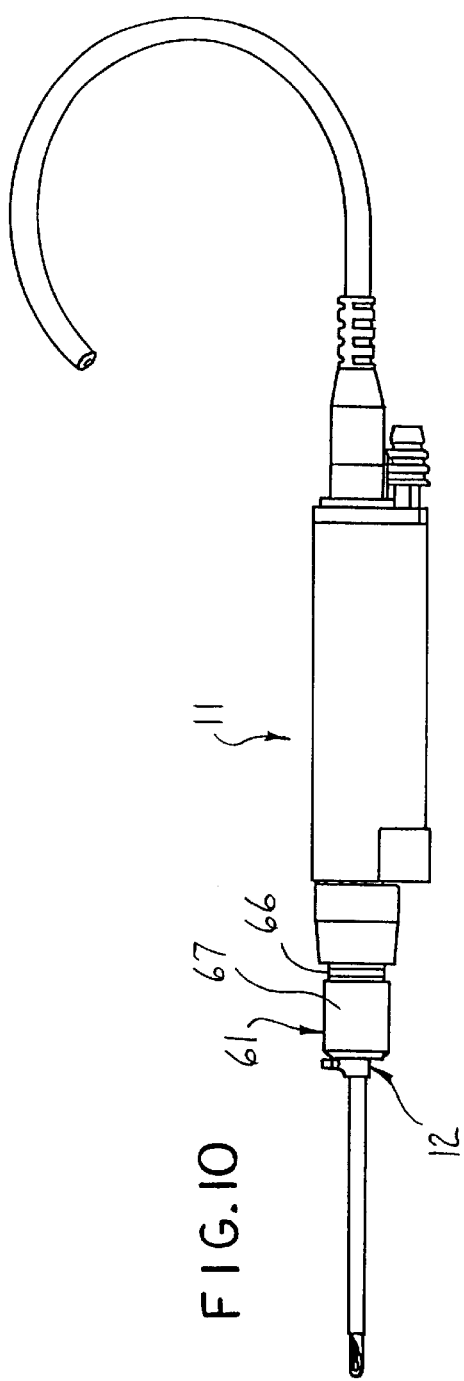

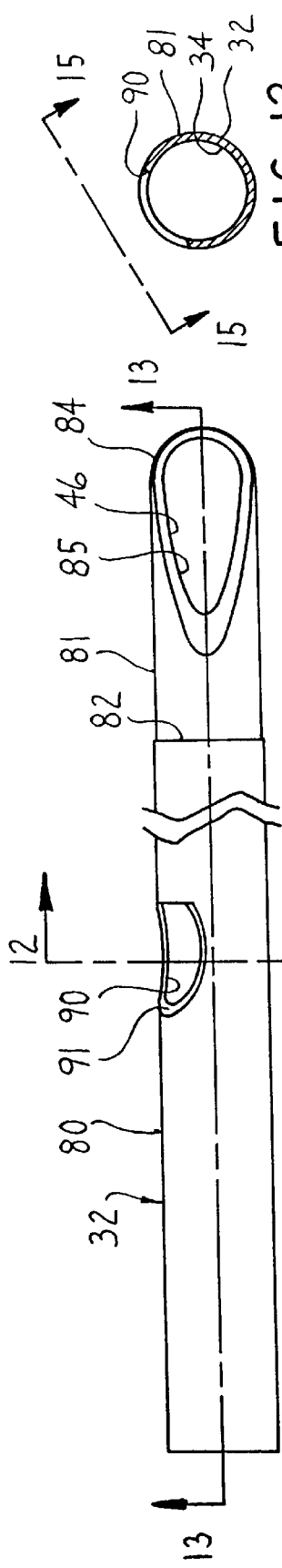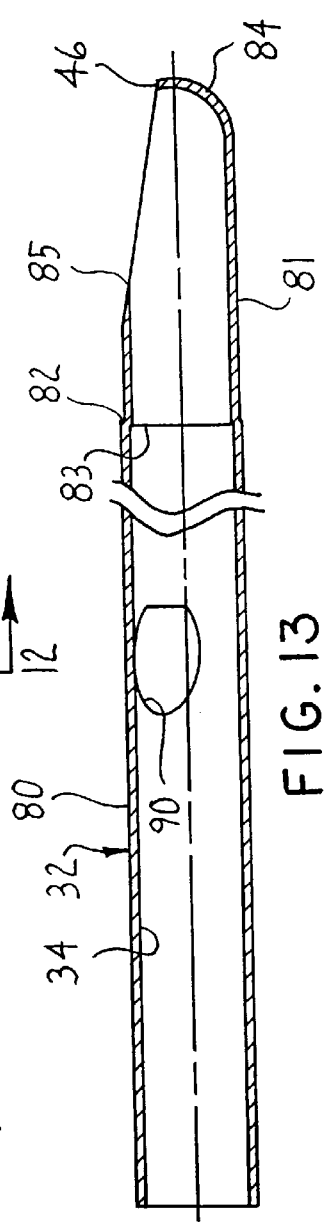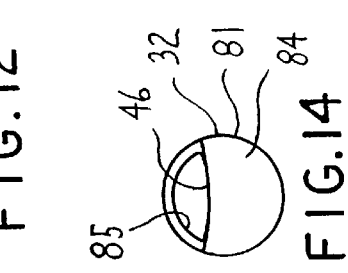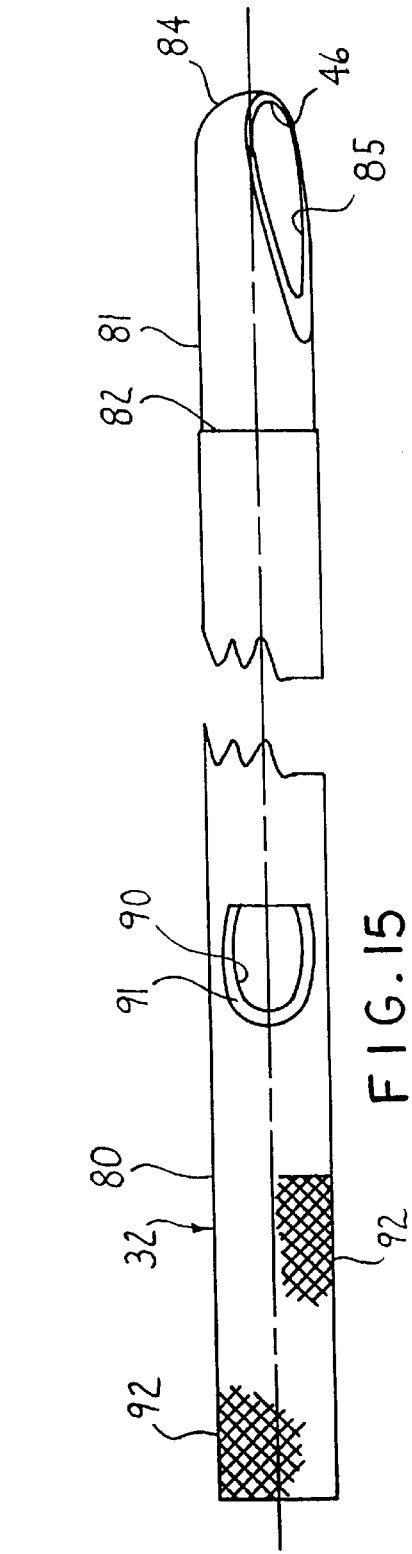

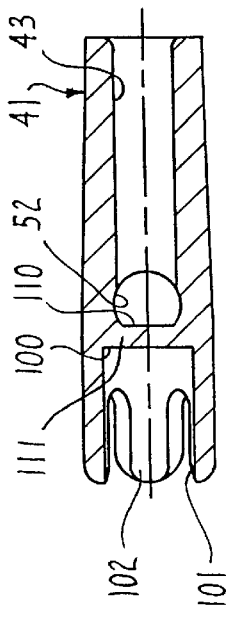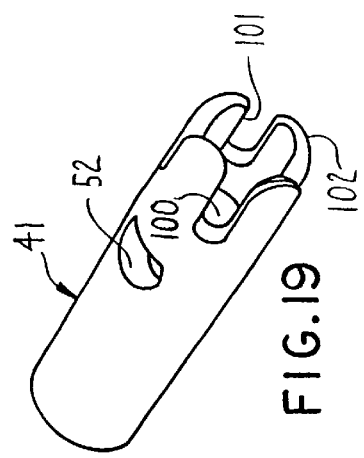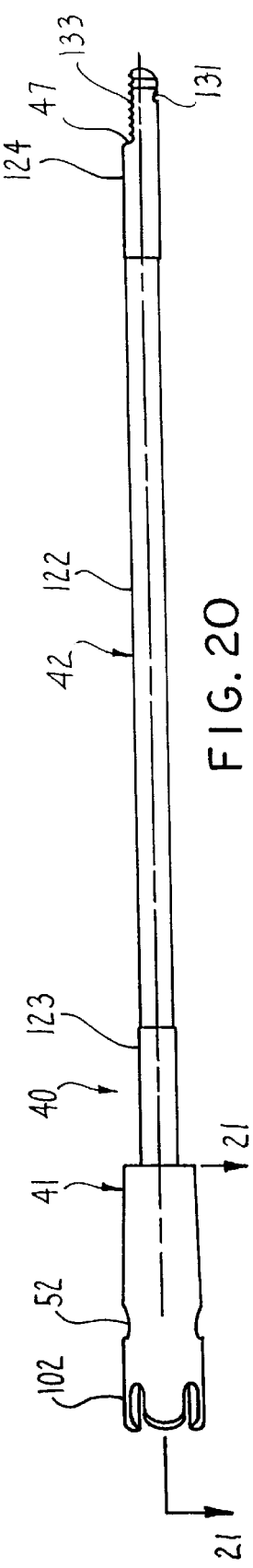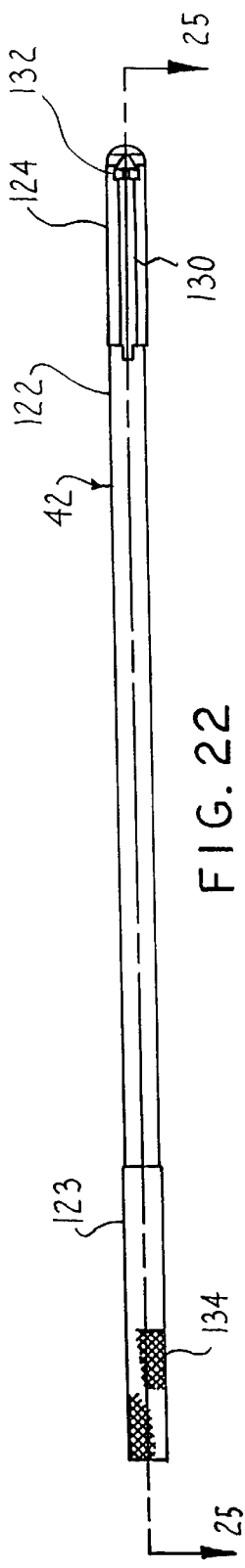

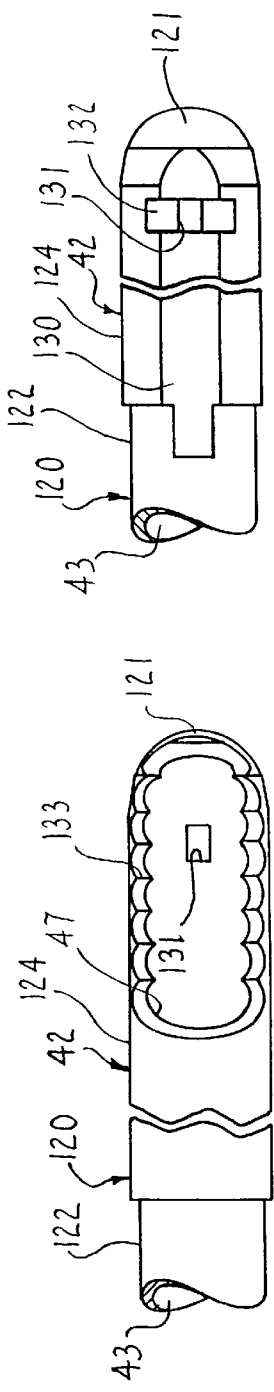
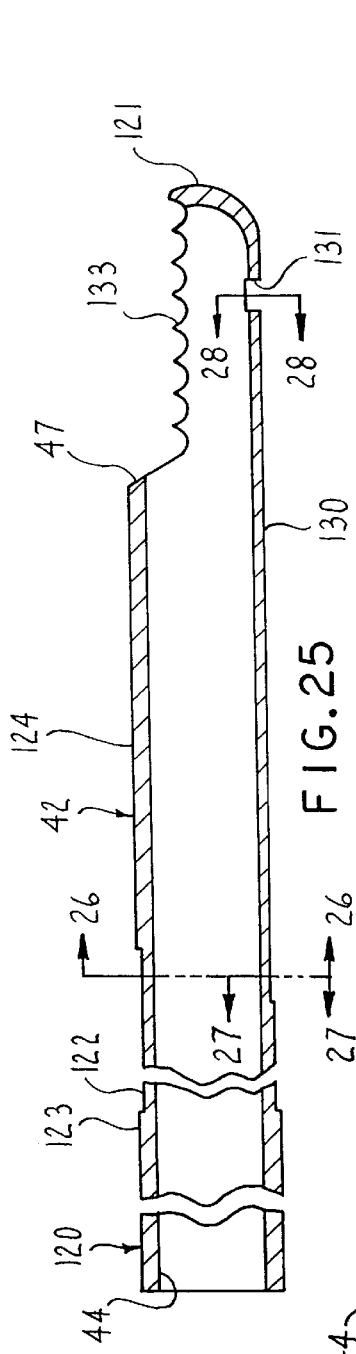
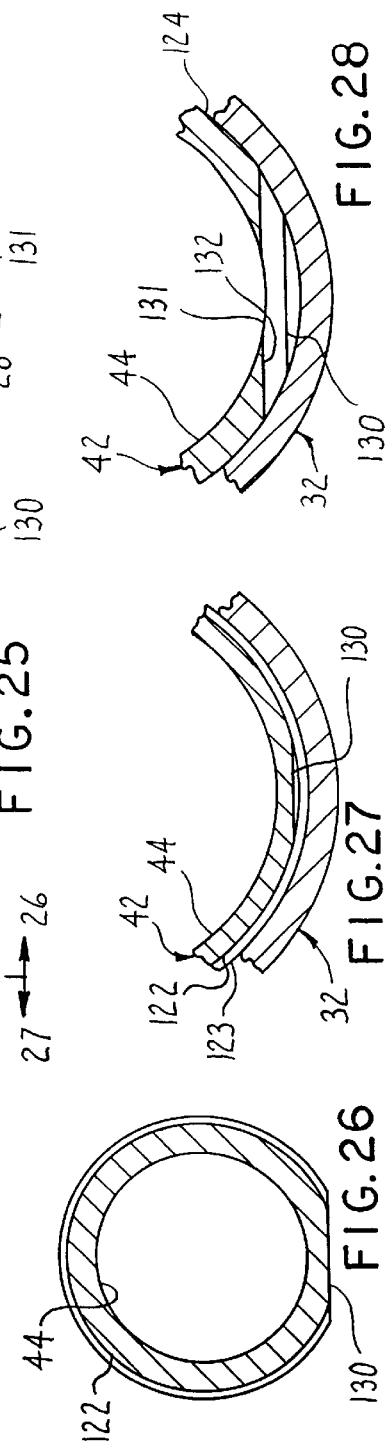
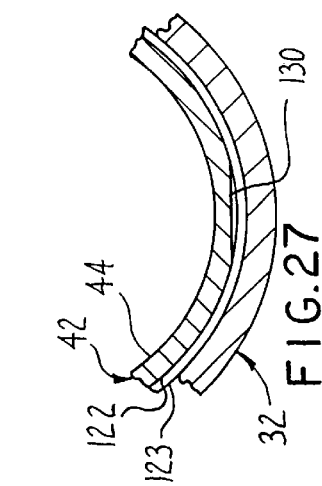
FIG. 23
FIG. 24
FIG. 25
FIG. 26
FIG. 27
FIG. 28

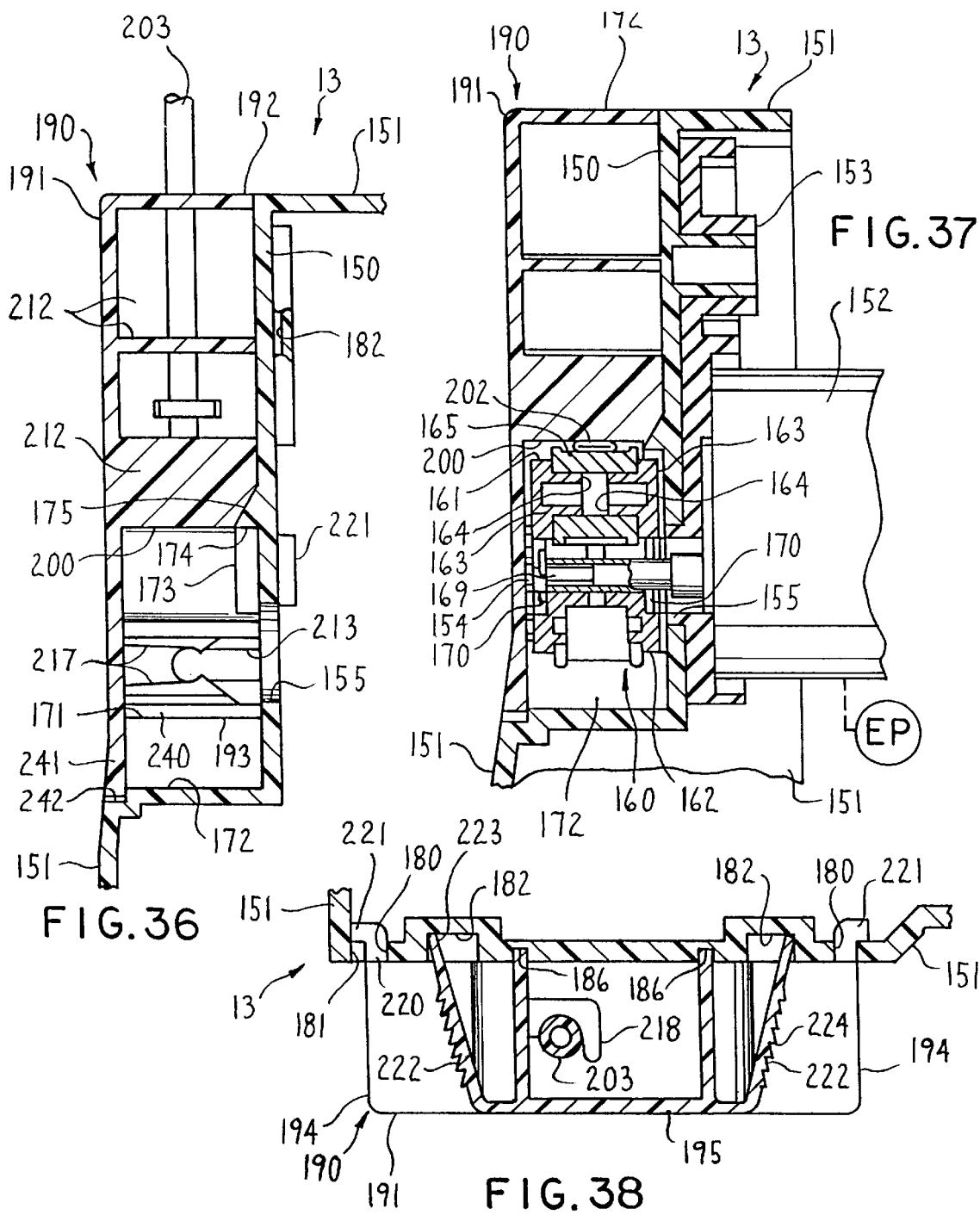

SURGICAL TOOL WITH INTEGRATED CHANNEL FOR IRRIGATION

RELATIONSHIP TO OTHER APPLICATIONS

This application is a continuation in part of U.S. patent application Ser. No. 09/318,299, filed May 25, 1999, now pending, which is a continuation of U.S. patent application Ser. No. 09/093,484, filed Jun. 8, 1998, now U.S. Pat. No. 5,928,257, which is a divisional of U.S. patent application Ser. No. 08/713,434, filed Sep. 13, 1996, now U.S. Pat. No. 5,792,167. The above-identified applications and patents are fully incorporated by reference into this patent.

FIELD OF THE INVENTION

This invention relates generally to surgical tool designed to be used with a complementary irrigation system. More particularly, this invention relates generally to a relatively small surgical tool especially suited for micro surgical procedures and/or pediatric surgical procedures.

SUMMARY OF THE INVENTION

The present invention relates in one aspect to an irrigation surgical tool system including a motorized handpiece, a tool removably insertable therein, a console including a peristaltic pump rotor and a tube set including a cassette mountable on the console for coaction with the rotor to supply irrigation liquid to the tool. The invention relates in another aspect to a tool having a rotating inner tube within a fixed outer tube. An irrigation liquid passage between the tubes communicates with the inner tube and thence through tissue working windows in the inner and outer tubes with a surgical site for alternately supplying irrigation liquid to the surgical site and removing, by entrainment, of debris from the surgical site by means of suction in the inner tube.

Further objects and purposes of the invention will be apparent to persons acquainted with apparatus of this general type upon reading the following description and inspecting the accompanying drawings.

BRIEF DESCRIPTION OF THE DRAWINGS

FIG. 2 is a schematic cross-sectional view of the cutter of FIG. 1.

FIG. 3 is a view similar to FIG. 2 with irrigation but not suction applied.

FIG. 4 is an elevational view of the FIG. 1 cutter.

FIG. 5 is an enlarged fragmentary central cross section of the FIG. 4 cutter.

FIG. 5B is an enlarged fragment of FIG. 5 showing in cross-section a modified tool fragment, the modification including an annular seal interposed between the fixed and rotating hubs of the tool.

FIG. 6 is an enlarged fragmentary partially broken view of the FIG. 4 cutter.

FIG. 7 is an enlarged fragment of FIG. 5 showing in cross section a handpiece fragment for resiliently retaining the tubular mounting hub of the tubular outer housing.

FIG. 9 is an elevational view similar to FIG. 8.

FIG. 10 is an elevational view similar to FIG. 9 but showing the cutter and handpiece engaged in an operating position.

FIG. 11 is a fragmentary view of the outer tube of the cutter.

FIG. 12 is a sectional view substantially taken on the line 12—12 of FIG. 11.

FIG. 13 is a central cross-sectional view substantially taken on the line 13—13 of FIG. 11.

FIG. 14 is a right end view of the FIG. 13 outer tube.

FIG. 15 is a fragmentary elevational view of the cutter outer tube of FIGS. 11–14 taken generally along the line 15—15 of FIG. 12.

FIG. 19 is a pictorial view of a drivable rotor hub of the inner rotor of the FIG. 4 cutter.

FIG. 20 is an elevational view of the inner rotor of the FIG. 4 cutter.

FIG. 21 is an enlarged central cross sectional view substantially taken on line 21—21 of FIG. 20.

FIG. 22 is an elevational view of the inner tube of the FIG. 20 inner rotor, taken from the bottom thereof in FIG. 20.

FIG. 23 is an enlarged fragment of the forward end portion (rightward in FIG. 20) of the FIGS. 20 and 22 rotatable inner tube.

FIG. 24 is a view similar to FIG. 23 but taken from the opposite side thereof, namely from the bottom in FIG. 20 and showing an enlarged fragment of FIG. 22.

FIG. 25 is a central cross sectional view of the FIG. 23 inner tube forward end portion taken substantially on the line 25—25 of FIG. 22.

FIG. 26 is a transverse cross sectional view substantially taken on the line 26—26 of FIG. 25.

FIG. 27 is an enlarged fragmentary transverse cross sectional view substantially taken on the line 27—27 of FIG. 25.

FIG. 28 is an enlarged fragmentary transverse cross sectional view substantially taken on the line 28—28 of FIG. 25.

FIG. 36 is a sectional view substantially taken on the line 36—36 the FIG. 35 with the cassette installed on the console.

FIG. 37 is a view similar to FIG. 36 but with a pump cassette installed in pumping position on the console mounting face.

FIG. 38 is a cross-sectional view substantially taken on the line 38—38 of FIG. 35 with the cassette installed on the console.

DETAILED DESCRIPTION

Figure 1:
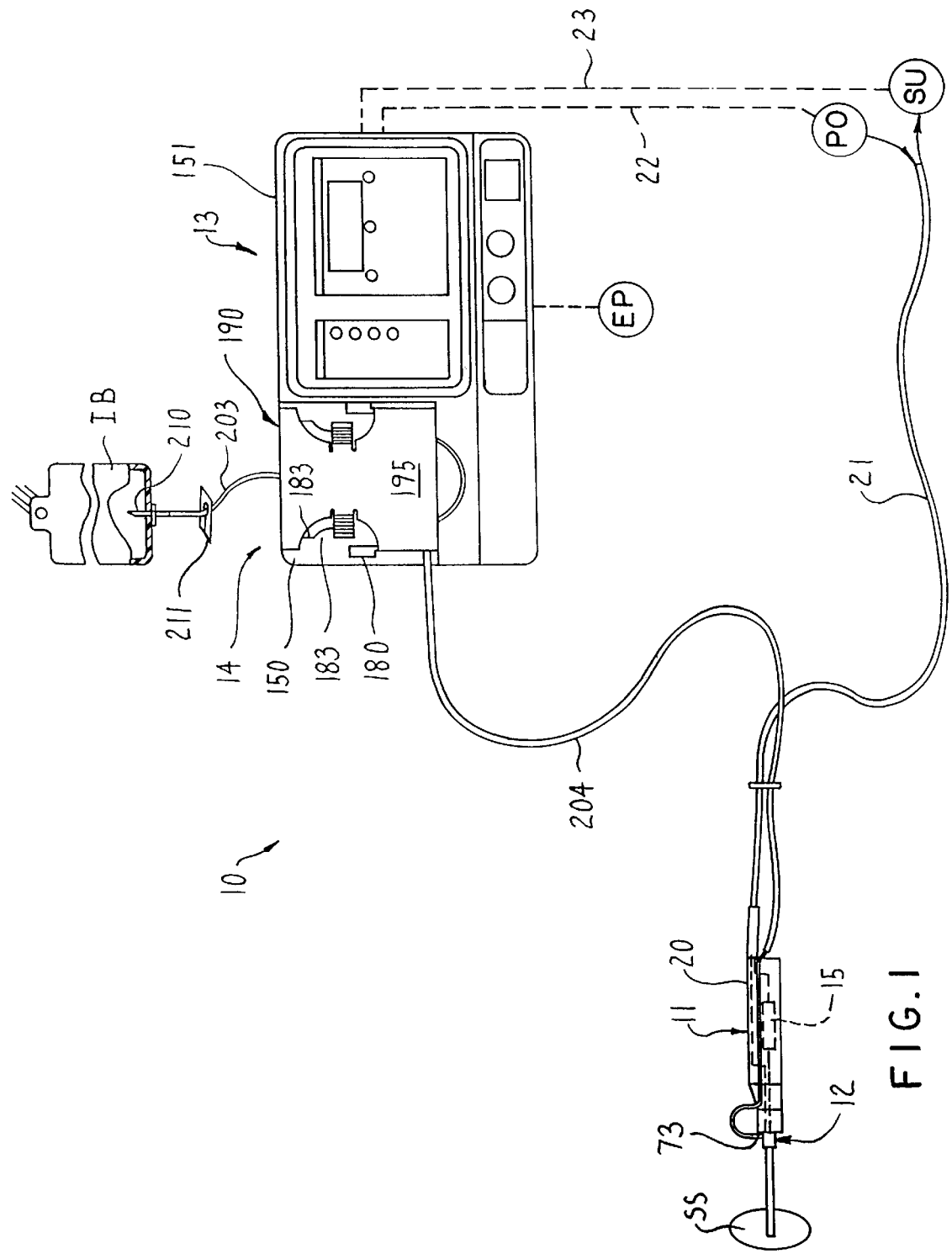
FIG. 1 is a somewhat schematic view of a surgical irrigation pump system embodying the invention.

An irrigation cutter system 10 (FIG. 1) comprises a motorized handpiece 11 removably supporting and driving a tool 12 insertable into a surgical site SS for working (e.g. cutting) patient tissue in the surgical site. The system 10 further includes a console 13 preferably located remote from the handpiece 11 and surgical site SS and a tube set 14 removably connectable with the console 13 and cooperable therewith for pumping irrigation liquid from a conventional irrigation liquid source, such as a conventional bag IB, to the handpiece 11. The handpiece 11 may be substantially conventional and, for example, similar to cutter handpieces marketed by Stryker Corporation under the trademark HUMMER I.

Thus, the handpiece 11 includes a power rotation source (e.g. electric motor), 15 indicated schematically in dotted lines in FIG. 1, contained in a hand held casing 20. The handpiece is supplied operating power for its powered rotation source 15 from any convenient power source schematically indicated at PO, such as a conventional electric power source of the type used to operate conventional surgical powered handpieces. The handpiece 11 is here provided with an internal suction path by which it can apply suction to the tool 12 in a substantially conventional manner, from a suitable suction source SU, as schematically indicated in dotted line in FIG. 1. The power source PO can and suction source SU may be connected to the handpiece 11 in any conventional manner, as in FIG. 1 through a common flexible cable 21 containing side by side insulated electric wires and a suction hose, not shown, or through separate flexible electrical cable and suction hose runs. The power source PO be controlled (e.g. turned on and off or varied) in any conventional manner, either directly by the user, or, as indicated schematically by the dotted line at 22, by suitable controls on the console 13 and operable by the user.

A tool 12 embodying the invention is shown in elevation in FIG. 4 and schematically in cross section in FIGS. 2 and 3. FIGS. 2 and 3 schematically show the basic parts of the tool 12. The tool 12 here comprises a tubular radially outer housing 30 including a tubular mounting hub 31 for fixed but releasable mounting on the forward portion of the casing 20 of the handpiece 11 and an outer tube 32 fixedly projecting forward from the mounting hub 31. The mounting hub and outer tube have communicating coaxial bores 33 and 34 defining a common radially outer passage 35.

The tool 12 further includes a tubular radially inner rotor 40 including a rotor hub 41 rotatably drivable by the power rotation source 15 of the handpiece 11 (FIG. 1), and an inner tube 42 fixedly projecting forward from the rotor hub 41. The rotor hub and inner tube have communicating coaxial bores 43 and 44 defining a common radially inner fluid passage 45.

The inner tube 42 is rotatably housed in the outer tube 32 and associated outer tubular mounting hub 31, extending axially from substantially the front (right in FIGS. 2 and 3) end of the outer tube 32 rearwardly (leftwardly in FIGS. 2 and 3) to the outer tubular mounting hub 31, to coaxially fixedly engage the rotor hub 41.

Although it is contemplated that the present invention may be applicable to surgical tools of different kind, in the particular embodiment shown the forward ends of the outer and inner tubes are at least partially closed (here providing an end thrust bearing effect therebetween), and the front end portions of such outer and inner tubes are each provided with sidewardly and/or radially opening, circumferentially alignable, patient tissue engaging windows, namely an outer window 46 and an inner window 47. In the particular embodiment shown, at least one window 46 or 47 has a cutting edge for cutting patient tissue upon rotation of the inner tube 42 within the outer tube 32. The rotation of the inner tube with respect to the outer tube thus periodically substantially radially aligns the inner window 47 with the outer window 46 and allows, at that time, communication between the inner fluid passage 45 and outer window 46.

The rotor hub 41, as schematically shown in FIGS. 2 and 3, has a hole 52 opening from the bore 43 which communicates through the handpiece 11 with the suction source SU as schematically shown in, and discussed above with respect to, FIG. 1.

To the extent above described, the tool 12, in its embodiment here shown, is substantially similar to conventional endoscopic suction cutters.

Turning now in more detail to the hollow outer housing 30, its mounting hub 31 (FIGS. 6 and 16–18) is conveniently constructed as a molded plastics member and is substantially rigid. The mounting hub 31 externally comprises a substantially cylindrical rear portion 53, an annular groove 54, a circumferential rib 55 and an elongate, somewhat forwardly tapering, forward portion 56. The annular groove 54 is occupied by a resilient seal ring, here a conventional O-ring 57, which protrudes radially outwardly therefrom for sealing engagement against a bore periphery in the front end, or chuck portion, 61 (FIG. 7) of the handpiece 11, for preventing leakage of liquid from the surgical site rearward along the outside of the mounting hub into the handpiece 11. It will be understood that the chuck portion 61 of the handpiece 11 is shown somewhat schematically to more clearly illustrate the features of the invention.

In the preferred embodiment shown, the tool 12 is chucked in the handpiece chuck 61 by displacing axially the outer chuck part 67 rearward against a spring 66 back by the handpiece casing 20 (FIG. 7). The chuck portion 61 includes a bore 62 which then receives the rear portion 53 of the fixed mounting hub 31 (as well as the portion of the inner rotor 40 to the rear thereof). Rearward displacement of the tool 12 with the respect to the chuck portion 61 is positively stopped by abutment of the rear face of the circumferential rib 55 against a forward facing step 63 defining the rear end of a forward opening recess 64 communicating with the forward end of the bore 62. Thus the chuck recess 64 rearwardly receives the rib 55 fully thereinto. The chuck 61 here illustrated includes a latch member 65 (here for example a ball) normally cammed radially inward by a ramp on the surrounding outer chuck part 67 with part 67 normally urged forward by the spring 66. However, with the outer chuck part 67 displaced rearward from its FIG. 7 position, the ball 65 can float radially out beyond the perimeter of the tool ridge 55. Thus, upon rearward insertion of the tool 12 in the chuck portion 61, the ridge 55 easily pushes the ball 65 radially outward out of the way to allow such ridge 55 to move into rearward abutment with the chuck step 63. The user then releases the chuck outer part 67 and the latter is displaced forward its FIG. 7 position by the spring 66, thus positively camming the ball 65 radially inward to its FIG. 7 position in front of the circumferential rib 55 of the tool 12. The front edge of the circumferential rib 55 is provided with circumferentially spaced substantially spherical notches 71 (FIGS. 6, 7 and 16) shaped and sized to receive the rear, radially inner portion of the ball 65, so as to urge the tool 12 rearward against the chuck step 63 and retain the tool 12 axially and circumferentially fixed in place in the chuck.

To remove the tool 12 from the chuck, one need merely again displace the chuck part 67 rearward, then displace the tool 12 forward (the circumferential rib 55 camming the floating ball 65 radially outward out of its way) and release the chuck part 67.

The notches 71 prevent inadvertent rotation of the tool mounting hub 31 within the handpiece 11 due to interference with the ball 65 with the unnotched portions 72 of the forward edge of the circumferential rib 55.

Figure 16:
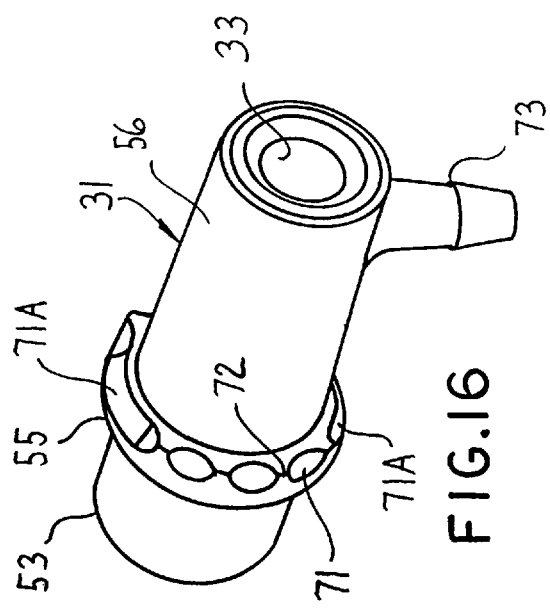
FIG. 16 is a pictorial view of the tubular mounting hub of the outer housing of the FIG. 4 cutter.

In the embodiment shown, one of the notches 71, namely one indicated at 71A in FIG. 16, is circumferentially elongate to permit limited angular displacement of the mounting hub 31 with respect to the handpiece, if the circumferentially elongate notch 71A is the one engaged by the ball 65.

It is contemplated that more than one radially inwardly resiliently biased ball 65 may be supplied and in the embodiment shown, three such balls are preferably provided in evenly circumferentially spaced (e.g. 120°) relation. As seen in FIG. 16, two circumferentially spaced elongate notches 71A are provided in the circumferential rib 55.

The mounting hub 31 has a substantially radially outward extending hollow fitting, here in the form of a nipple 73 (FIGS. 5, 6 and 16), near the front end thereof and spaced forward from the circumferential rib 55 and handpiece chuck portion 61 (FIG. 10). The fitting 73 includes a through passage 74 for irrigation liquid, extending through the radially outer end of the nipple 73 and thence radially inward therefrom into the central bore 33 of the mounting hub 31. See also FIG. 17. The outer end of the nipple 73 is connectable to communicate with an outflow hose portion, hereafter described at 204, of the tube set 14 (FIG. 1).

Figure 17:
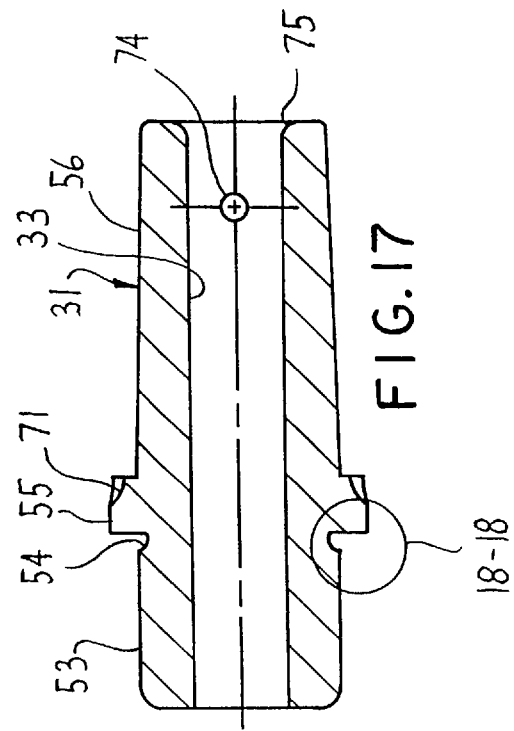
FIG. 17 is a central cross-sectional view thereof.
Figure 18:
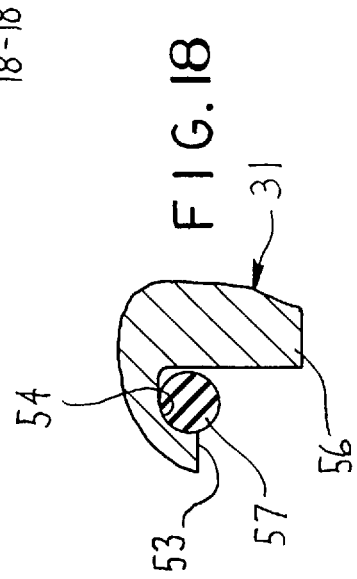
FIG. 18 is an enlarged fragment, indicated at 18—18 of FIG. 17.

The front end of the bore 33 is chamfered as indicated at 75 in FIG. 17 to facilitate installation of the rear end of the outer tube 32 rearwardly into the bore 33 of the mounting hub 31 to allocate same therein in the manner indicated in FIGS. 5 and 6.

The outer tube 32 (FIGS. 11–15) comprises an elongate cylindrical rearward portion 80 from which forwardly coaxially extends a substantially shorter hollow tubular nose piece 81. The nose piece 81 has slightly lesser inner and outer diameters than the elongate cylindrical rearward portion 80 and is joined thereto by any convenient and conventional means, for example, integrally, as by radially inwardly deforming the nose piece, or by laser welding or the like of initially separate pieces 80 and 81. The joinder defines circumferential external and internal steps 82 and 83 (FIG. 13). While the front end of the nose piece 81 may be configured as desired, in the embodiment shown it is convexly rounded forward in a generally spherical manner as indicated at 84. Although the nose piece can be configured to perform a variety of surgical, patient tissue working operations, in the particular unit shown, the nose piece 81 is provided with a sloped planar relief defining the angled shearing outer window 46, same being provided with a sharp shearing edge 85 for shearing coaction with the above mentioned inner window 47 of the inner tube 42 hereafter discussed. The radial interior diameter reduction, or necking in, of the nose piece 81 with respect to the rearward cylindrical portion 80, provides a close radial shearing fit with the exterior of the front portion of the inner tube 42.

The elongate cylindrical rearward portion 80 of the outer tube 32 includes an irrigation liquid inlet port 90 (FIGS. 11 and 12) axially positioned to align with and be centered on the irrigation liquid through passage 74 of the nipple 73, when the mounting hub 31 is assembled on the outer tube 32. The irrigation liquid inlet port 90 is preferably substantially D-shaped, with the straight edge of the D-shape at the forward end of the port 90 and the curved portion of the port 90 extending rearward therefrom. The hole 90 is preferably formed in the outer tube 32 by wire EDM or, any other convenient means, such as by transverse (chordal) milling, with an appropriately shaped milling wheel perimeter cross section. The substantially D-shaped configuration of the port 90 facilitates snug telescoping of the rigid plastics mounting hub 31 over the rear end portion of the outer tube 32 during assembly by reducing any tendency of the edges of the hole 90 to gouge the inside of the mounting hub during relative axial motion therebetween as assembly is being carried out. It should, of course, be realized that port 90 may have a shape different from what has been described.

In the preferred embodiment, a heated metal outer tube 32 is pressed coaxially forward or rearward into a somewhat undersized bore 33 in a thermoplastics material mounting hub 31, which provides, after the metal tube cools, a rigid fixed coaxial joinder between tube 32 and hub 31.

Given a mounting hub 31 of thermoplastic material, insertion of a heated metal outer tube 32 tends to soften the engaged portion of the thermoplastics mounting hub to allow easy pressed insertion of tube into mounting hub, whereafter cooling of the tube allows the mounting hub to recontour its inner bore to closely fit and harden about the cooled metal tube. To further facilitate fixed connection of tube to hub, it may be desired to externally knurl, or otherwise surface roughen, the rear end portion of the outer tube 32 in spaced relation to the rear of the hole 90, as for example schematically and partially indicated at 92 in FIG. 15. Alternately, the knurling is extendably over the entire area in contact with the hub 31.

Upon rearward sliding of the rear end of the heated metal outer tube 32 into the bore 33 of the mounting hub 31, the sloped curved edge 91 of the rear portion of the hole 90 tends to slide rearward easily past the rear end of the through passage 74 (FIG. 6) without risk of distorting or partially closing same and so avoids the risk of reducing irrigation flow cross section through the assembled housing 30.

Turning now to the inner rotor 40 in more detail, the rotor hub 41 (FIGS. 19–21) has a preferably cylindrical, rear opening coaxial recess 100. The rear part of the recess 100 has diametrally opposed rear opening notches 101 (here two pair thereof) separated by rear extending fingers 102. The rear ends of fingers 102 are preferably rounded, at least in their radially outer parts and in the rear end portions of the notches 101.

Generally in the manner shown in U.S. Pat. No. 5,192,292, assigned to the assignee of the present invention, a coil compression spring 103 (FIG. 4) is received in and protrudes rearwardly (when at rest) from the recess 100 peripherally walled by the fingers 102. With the tool 12 chucked in the handpiece 11 (FIG. 1), the front end 104 of the shaft of the powered rotation source 15 inserts into the rotor hub recess 100 (FIG. 4) to compress the spring and thereby urge the inner rotor 40 forward with respect to the housing 30. A diametral cross-pin 105 has outer ends received in diametrally opposed ones of the notches 101 for rotatably driving the circumferentially flanking ones of the fingers 102 and thereby rotating the inner rotor 40.

The suction hole 52 in some preferred versions of the invention is substantially D-shaped, as seen in FIG. 21, with the flat edge 110 thereof rearmost and separated from the rear recess 100 by a transverse wall 111 which may thus be diametral, flat, and relatively thin. As seen in FIG. 5, the suction hole 52 extends diametrally through the rotor hub and the rear end portion of the inner tube 42 extends rearwardly part way into the suction hole 52 for direct communication of the suction bore 44 of the inner tube 42 with the transverse suction hole 52, and thereby with the suction source SU when the tool 12 is chucked in the handpiece as seen in FIG. 1.

The inner tube 42 comprises an elongate substantially cylindrical rearward portion 120 carrying a coaxial front end portion 121, which in a particular unit shown is closed except at the front portion of the window 47, the latter being formed in the elongate cylindrical portion 120, as seen in FIGS. 23 and 25. In the embodiment shown, the interior surface of the elongate cylindrical portion 120 defines the bore 44 and is substantially cylindrical, and hence of substantially constant diameter, throughout its length.

In contrast, the elongate intermediate outer periphery 122 of the inner tube 42 is of diameter reduced from, but coaxial with, the rear and front outer peripheral portions 123 and 124 of the periphery 122. Rear and front portions 123 and 124 act as rear and front radial thrust bearings, respectively, to rotatably support the inner tube 42 within the outer tube 32.

The front radial thrust bearing portion 124 is circumferentially interrupted by a longitudinal irrigation liquid channel 130 which communicates from the intermediate outer peripheral portion 122 of the inner tube substantially to the inner tube front end. An irrigation liquid port 131 (FIGS. 23–25) extends through the peripheral wall of the front outer peripheral portion 124 and communicates between the bore 44 of the inner tube and the longitudinal irrigation liquid channel 130. Preferably the port 131 is centered circumferentially on the channel 130 and both are diametrically opposed to the window 47. In the embodiment shown, the port 131 opens through the irrigation liquid channel 130 near the front end thereof and is spaced slightly rearward from the rounded front end portion 121.

In the preferred embodiment shown, the channel 130 is conveniently an axially elongate chordal flat in the outer periphery of the forward portion 124, which flat 130 extends rearward somewhat into the intermediate peripheral portion 122 of the inner tube and is of sufficient radial depth as to flatten the periphery of the reduced diameter intermediate portion 122. The port 131 and channel 130 each can be formed by any convenient means, e.g. EDM or a simple tangential grinding or milling pass across the periphery of the inner tube.

The port 131 is conveniently formed by a chordal flat 132 incised sufficiently deeply into the periphery of the inner tube 42 as to open into the bore 44. The chordal flat 132 is circumferentially somewhat wider than, and axially much shorter than, the chordal flat 130.

Although windows 47 of various forms are contemplated, in the embodiment shown in FIGS. 23 and 25, the window 47 through most of its length extends substantially along a chordal plane of the inner tube 42 and occupies close to but less than half the circumference of the inner tube 42. Also in the embodiment shown in FIGS. 23 and 25, the chordal edges of the window 47 are provided with teeth 133 spaced longitudinally therealong.

The rear portion 123 of the inner tube 42 is telescopingly fixed in the front opening bore 43 of the rotor hub 41, as shown in FIG. 5, by any convenient means, for example in the manner above described with respect to fixing of the outer tube 32 in the mounting hub 31. For example, the rotor hub 41 is preferably of a thermoplastic material for receiving the heated rearward portion 123 of the inner tube 42 to, upon cooling, fixedly grip the latter. Again, to facilitate fixed gripping, the rearwardmost part of the inner tube rear portion 123 may be surface textured, as by knurling 134 (FIG. 22), if desired.

With the outer housing 30 and inner rotor 40 each assembled in the manner above discussed, the tool 12 can be assembled by simply inserting the inner tube 42 forwardly into the open rear end of the outer tube 32 and its surrounding mounting hub 31, in the manner generally indicated in FIGS. 4 and 5.

Figure 5A:
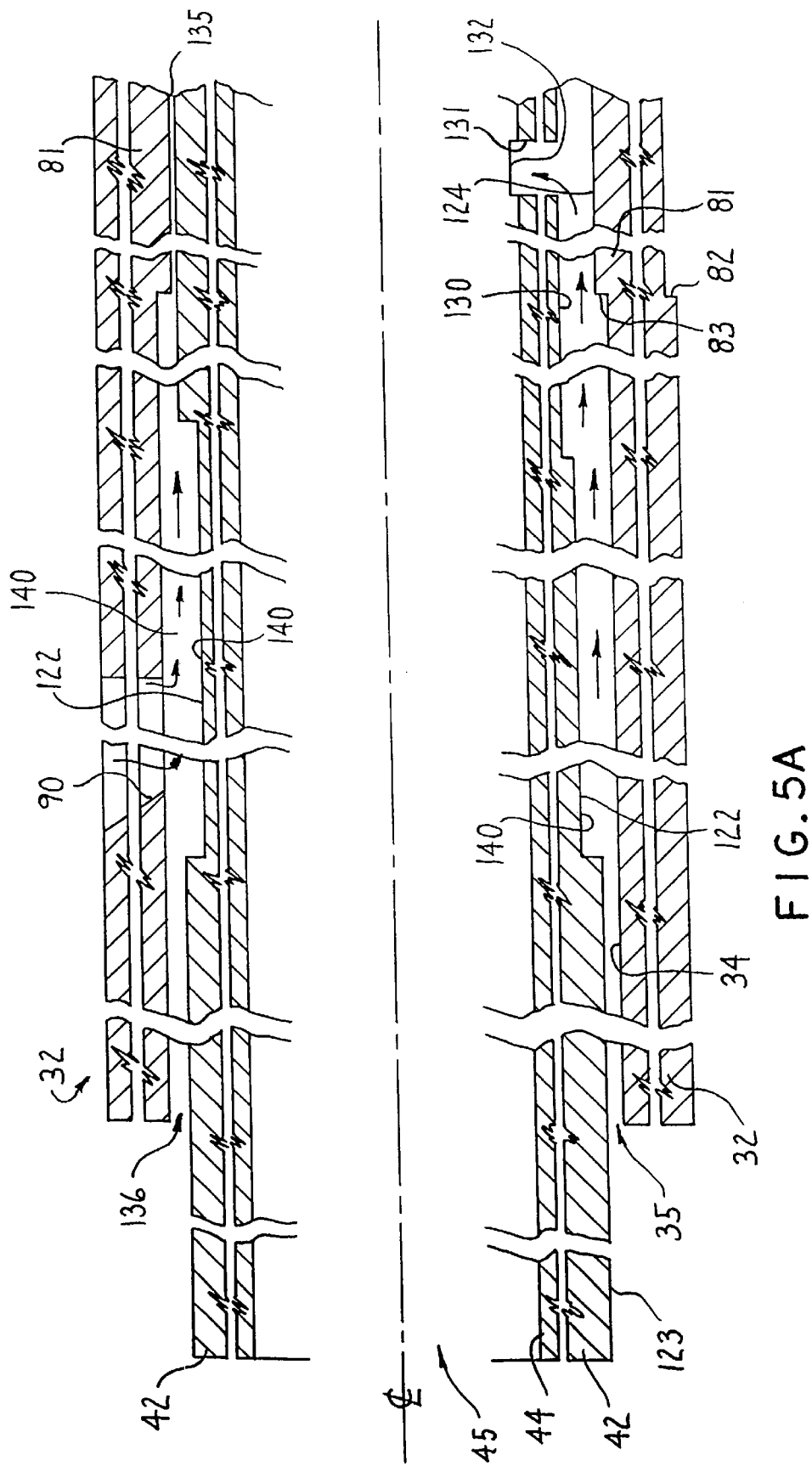
FIG. 5A is a fragmentary enlargement of FIG. 5.

When thus assembled, and as seen in larger size in FIG. 5A, the front end portion of the inner tube is supported by rotating bearing contact of its front outer periphery 124 by the inward stepped nose piece 81 of the outer tube 32 across the bearing clearance gap 135 of approximately 0.001 inch. The rearward portion 123 of the inner tube 42 is supported rotationally by the rear end portion of the outer tube 32 across a bearing clearance gap 136 of approximately 0.0035 inch. The irrigation liquid inlet port 90 of the outer tube 32 supplies irrigation liquid radially inward to an annular fluid passage 140 having a radial thickness of about 0.007 inch. Irrigation liquid flow is represented by the arrows in FIG. 5A and passes forward through the annular flow passage 140, then through the longitudinal irrigation liquid channel 130 formed by the corresponding chordal flat, and then forward beyond the step 83 in the outer tube 32 and radially inward through the port 131 into the interior of the inner tube 42.

The assembled tool 12 is chucked, as above discussed, with the tool circumferential rib 71 trapped behind the balls 65 (FIG. 7) to hold the outer housing 30 of the tool 12 fixed in the handpiece chuck 61 and wherein the rear end of the rotor hub 41 and its spring 103 engage the rotatable shaft 104 and its drive pin 105 in the manner discussed above with respect to FIG. 4, for rotating the inner rotor 40 with respect to the outer housing 30 of the tool.

Irrigation liquid flow, in accord with the arrows in FIG. 3, passes radially inward through the port 131 in the inner tube and into the forward portion of the interior thereof opposite the windows 46 and 47. If suction is not applied to the inner tube 42, the irrigation liquid then flows out through the rotating inner tube window 46 and fixed outer tube window 47 into the surgical site SS for supplying the latter with irrigation liquid.

On the other hand, when suction is applied to the rear end of the inner tube 42, as in FIG. 2, such suction tends to pull rearward, through the inner tube 42, irrigation liquid and entrained surgical debris drawn through the periodically radially aligned windows 46 and 47 from the surgical site.

Figure 8:
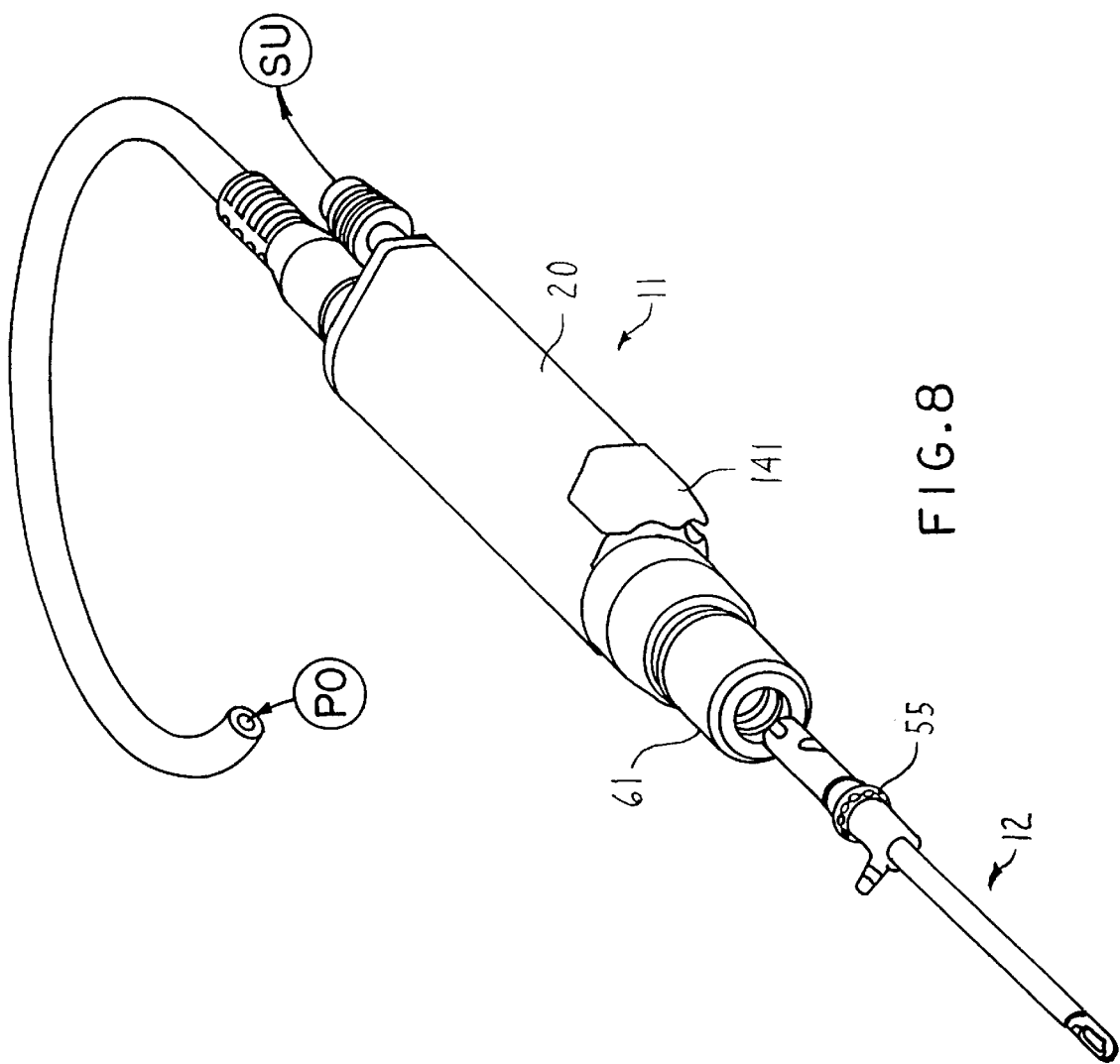
FIG. 8 is a fragmentary exploded view of the FIG. 1 handpiece and cutter, showing same positioned prior to insertion of the rear end of the cutter into the front end of the handpiece.

If desired, the handpiece 11 itself may be provided with the user operator control for controlling rotation of the tool 12 and/or suction in a conventional manner and for this purpose a user thumb actuable push button control 141 is shown in FIG. 8.

Figure 29:
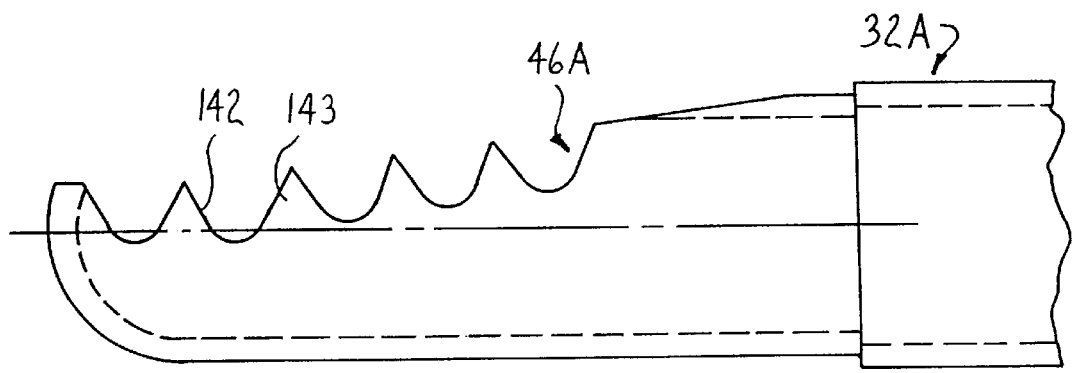
FIG. 29 is an enlarged fragmentary elevational view of the forward end of the fixed outer tube generally similar to the orientation of FIG. 13 but taken from the opposite side thereof and showing a modification of the cutting window.
Figure 30:
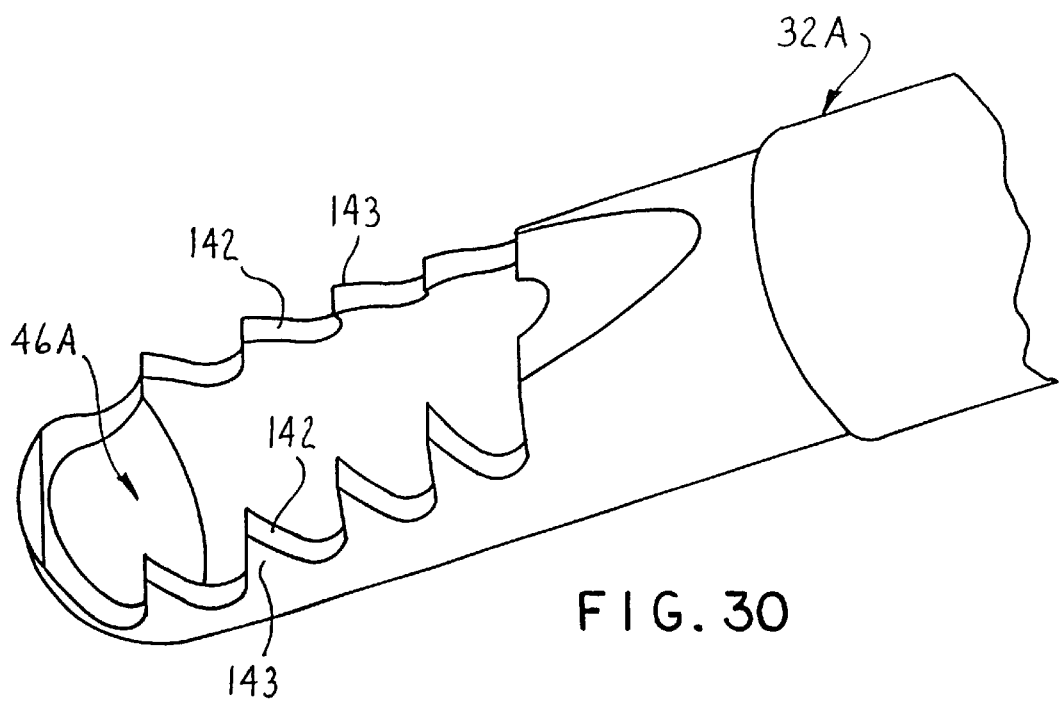
FIG. 30 is a pictorial view of the modified FIG. 29 device.

FIGS. 29 and 30 show a modified cutting window 46A of the fixed outer tube wherein the opposite sides of the window 46A of the outer tube 32A have a series of notches 142 formed therein, leaving the sides of the modified window 46A defined by a plurality of teeth separated by such notches 142. The teeth 143 coact with the teeth 133 in the window 47 of the rotating inner tube 42. It has been found by that the toothed window 46A of the modified outer tube 32A provides a more aggressive cutting action than the untoothed window 46 of the outer tube 32 of FIG. 15.

Irrigation liquid flow rearward from the irrigator inlet port 90 has not been significant, and thus is believed a result of the path of least resistance to irrigation flow being forward from the port. Thus, while no liquid seal rearward of port 90 has been needed, a modification is contemplated which, as shown for example in FIG. 5B, provides an annular seal member 144 (e.g. of Teflon™ or other conventional seal material) sealingly interposed between the fixed housing 30B and inner rotor 40B (here between the opposed ends of the fixed and rotating hubs 31B and 41B), behind the port 90 (FIG. 5).

Turning now more particularly to the console 13 and tube set 14, the console 13 (FIG. 35–38) includes a case 151 and a mounting plate 150 which forms a portion (the left front portion in FIG. 1) of the case 151. The mounting plate 150 is preferably of a rigid molded plastics material. The mounting plate 150 has a motor 152 (FIG. 37) mounted to extend fixedly rearwardly therefrom. The motor 152 is fixed on the mounting plate 150 through any convenient means, here including a fixed rigid carrier member 153. The motor 152 has a rotatable shaft 154 extending forward through a hole 155 in the mounting plate 150. A peristaltic pump rotor 160 is fixed on the shaft 154 for rotation therewith in front of the mounting plate 150.

In the embodiment shown, the rotor comprises axially opposed, preferably identical, generally triangular, front and rear roller carriers 161 and 162 (FIG. 37). The roller carriers 161 and 162 each comprise a substantially radially extending, generally triangularly plate 163 and plural (here 3) pairs of coaxially opposed stub shafts 164. In the embodiment shown, the carriers 161 and 162 are of molded plastic and the stub shafts 164 are recessed at their opposed free ends to minimize the amount of plastics material required. Each coaxially opposed pair of stub shafts 164 rotatably supports a generally spool-shaped, coaxial, peristaltic pump roller 165. The roller carriers 161 and 162 are fixed on the shaft 154 by any convenient means, for example by sandwiching axially between diametral through pins 170 fixedly diametrally extending from the motor shaft 154 adjacent front and rear ends of the shaft and engaging corresponding diametral depressions in the axially opposite sides of the plates 163. In this way, the carriers 161 and 162 are held against axial separation so as to reliably rotatably support the rollers 165 and are positively rotatably drive by the motor shaft 154 and thereby for orbiting the pump rollers 165 by rotation of the motor shaft 154. Thus, rotation of the motor shaft 154, in response to energization of the motor 152, rotates the peristaltic pump rotor 160 and thereby orbits the rollers 165 for peristaltic pumping with respect to the peristaltic pumping portion of the tube set hereinafter discussed.

To facilitate assembly, the front end of shaft 154 may be recessed and the front (outer shaft end) pin may be diametrally prefixed in an axial plug 169. The carriers 161, 162 and rollers 165 may first be installed on the motor shaft 154. Then, the pinned plug 169 is axially inserted and fixed (e.g. by adhesive) in the recessed front end of the motor shaft 154, to fix the carriers 161, 162 on the motor shaft 154.

The mounting plate 150 has a forward step 171 spaced below the pump shaft 154 (FIG. 35) with a concave semicircular hollow 172 below the rotor 160 and sized and shaped to loosely accommodate the orbiting rollers 165.

An arcuate cam 173 protrudes fixedly forward from the mounting plate 150. The cam 173 is semi-circularly concave toward the rotor 160 and hence longitudinally (in FIG. 35 downward) along the mounting plate 150. The concave face 174 of the cam 173 faces toward and extends circumferentially close along just outside the orbit of the rollers 165 of the pump rotor 160. On the other hand, the front face 175 of the cam 173 is a sloping ramp-like surface angled to face forward and longitudinally away from the rotor 160 (upward in FIG. 35) for purposes appearing hereafter.

The mounting plate 150 (FIG. 35) has parallel, longitudinally extending (extending vertically in FIG. 35), laterally spaced slots 180 therethrough. The bottom portions of the slots 180 are spaced on opposite sides of the cam 173 and extend at least to the bottom thereof (here slightly below same). Substantially at the level of the top of the cam 173, the slots 180 widen away from each other to form widened mouths 181.

Recesses 182 in the front face of the mounting plate 150 are well spaced above the cam 173 and extend upward in slightly vertically overlapping fashion above the slots 180. The recesses 182 are laterally spaced from each other and laterally spaced inboard of the slots 180. The space between the recesses 180 is approximately the width of the cam 173, here slightly greater. The recesses 182 have laterally opposed, laterally inwardly projecting, wedge shaped portions 183, including laterally inward and upward facing, angled ramps 184 terminating in downward facing steps 185.

The mounting plate 150 also has laterally spaced, parallel, longitudinally aligned, guide grooves laterally spaced closer to the recesses 182 than to each other, longitudinally overlapping both the recesses 182 and slots 180, and overlying, in vertically spaced relation, the cam 173.

The tube set 14 includes a cassette 190 (FIGS. 1 and 31–34). The cassette has a body 191 having longitudinally spaced top and bottom ends 192 and 193 and laterally spaced sides 194. The body 191 has a plate-like front wall 195 bounded by the ends 192 and 193 and sides 194. The body 191 includes a concave backing wall 200 (FIGS. 32 and 34) which extends rearward from the front wall 195 thicknesswise of the body 191. The concave backing wall 200 is semi-circular and opens concavely toward one end of the body, here the bottom end 193.

Figure 32:
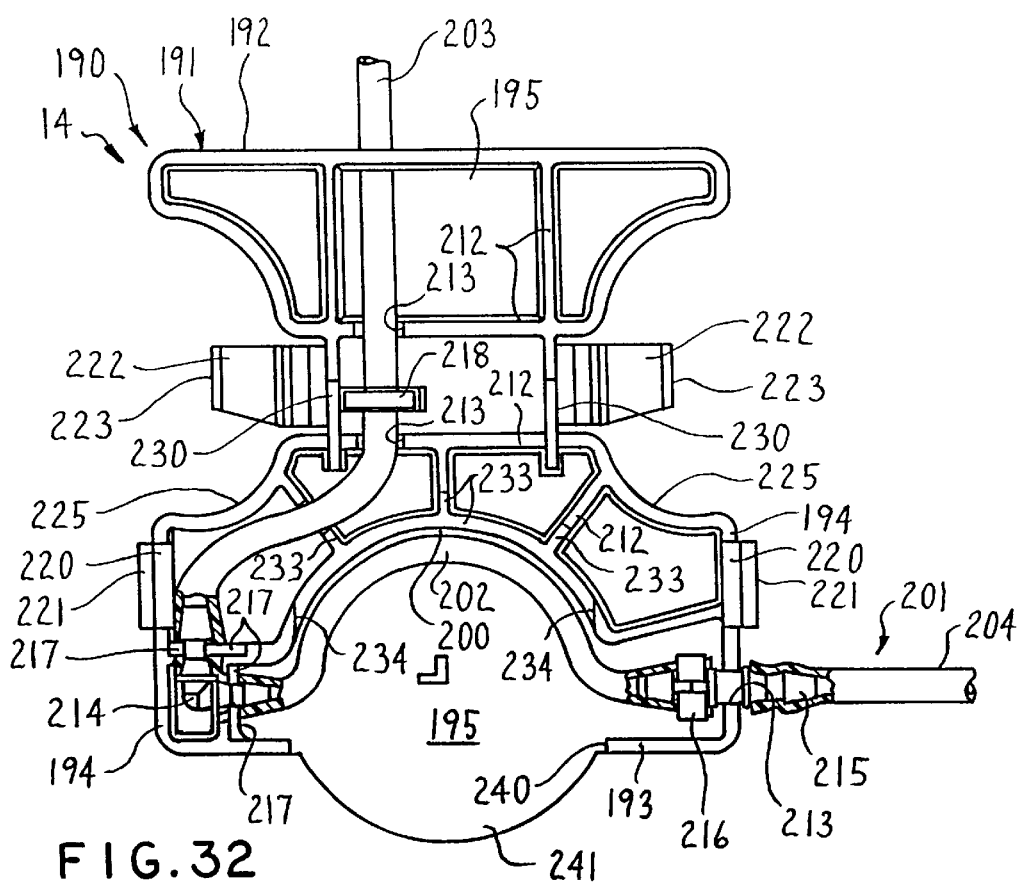
FIG. 32 is a rear view of the FIG. 31 cassette.
Figure 34:
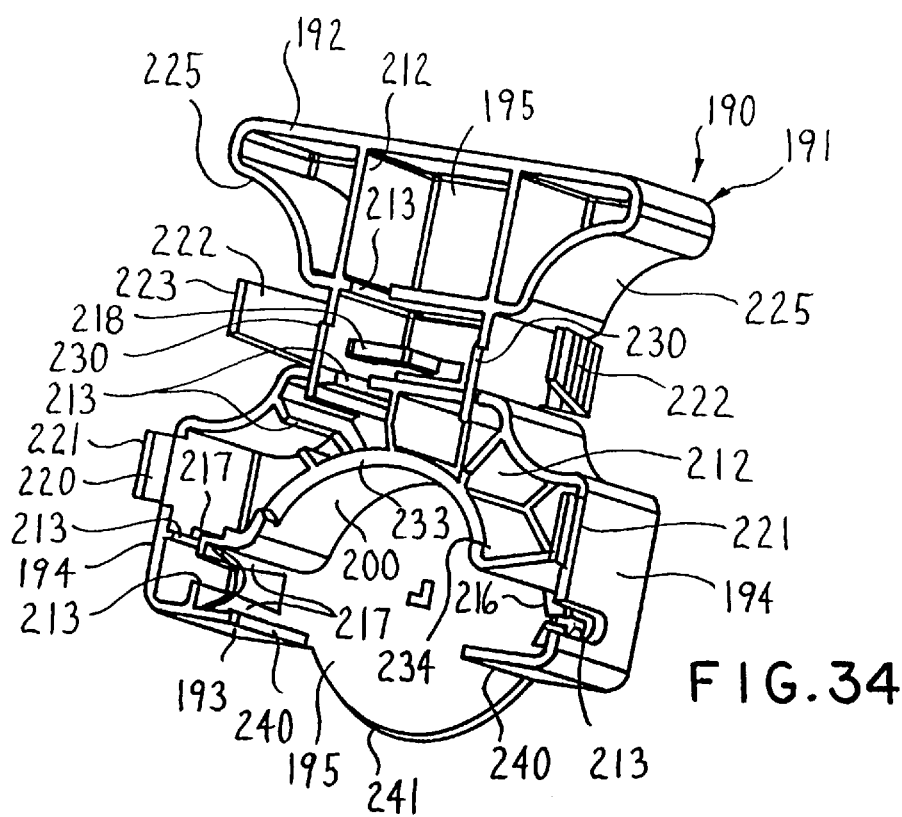
FIG. 34 is a similar pictorial view of the rear of the FIG. 33 cassette showing primarily the rear and left side thereof.
Figure 35:
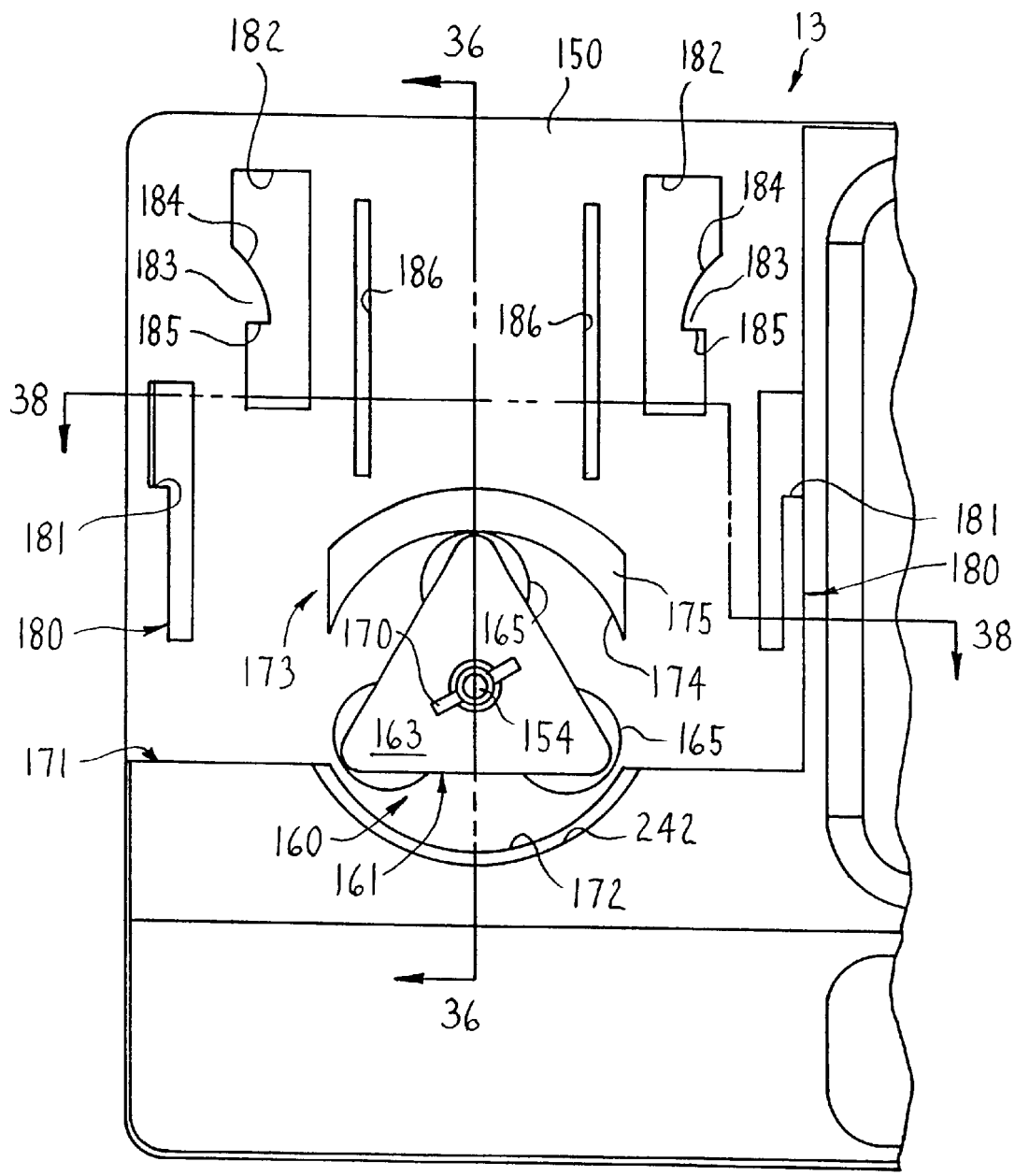
FIG. 35 is a fragmentary front view of the FIG. 1 console showing the peristaltic pump mounting plate with the FIGS. 1 and 31 cassette removed.
Figure 39:
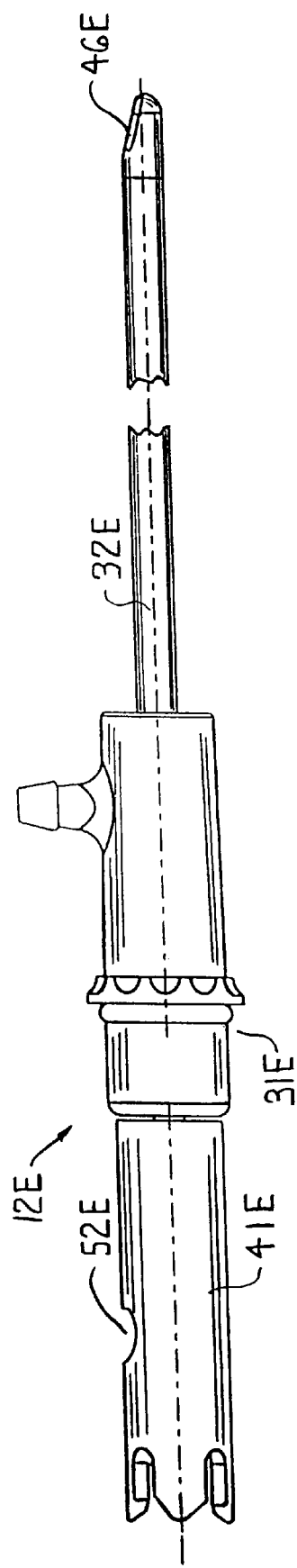
FIG. 39 is an elevational view of an alternative cutter of this invention.
Figure 41:
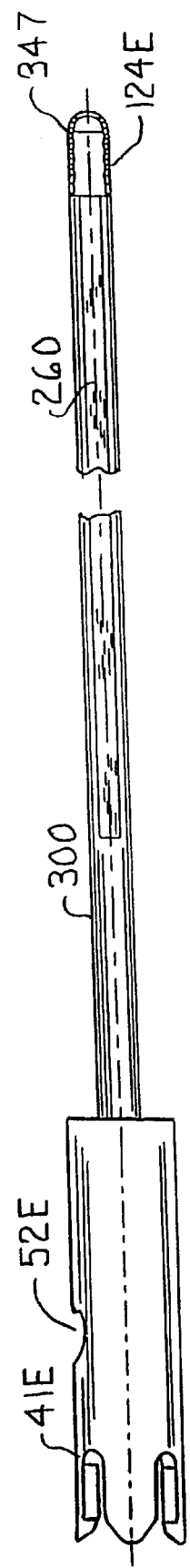
FIG. 41 is an elevational view of the inner tube of the FIG. 39 cutter.

The cassette body, as seen from the rear in FIGS. 32 and 34, is provided with plural reenforcing ribs 212 extending rearward from the front wall 195 to provide adequate strength to the body 191 while limiting the amount of material required. Such body is preferably formed by molding of a suitable plastics, hardenable material.

A peristaltic pumping hose 201 (FIG. 32) has a pumping portion 202 backed by the concave backing wall 200 and inflow and outflow portions 203 and 204 respectively extending from the cassette 190 and flanking the pumping portion 202. The inflow portion 203 of the pump hose 201 is provided with a suitable connector 210 at its free, upper end, for connection in a conventional manner to a irrigation liquid source such as the irrigation liquid bag IB in FIG. 1 and may be provided with a conventional removable clamp 211 for controlling flow from the bag IB.

The inflow hose portion 203 is led down into the cassette body 191 through a hole 205 in the cassette body top wall 192. An L-shaped keeper bar 218 (FIGS. 32 and 34) fixedly extends from one side wall 194 of the body 191 (the left side wall in FIGS. 32 and 34) intermediate the top most two lateral ribs 212 and opens forward toward the hose portion 203 to prevent its rearward escape from the adjacent notches 213. The inflow hose 203 is led through notches 213 in various of the ribs 212 down and to one side (the left in FIG. 32) of the downward opening concave backing wall 200 and sealingly and fixedly connects to an elbow 214 at one of the notches 213 in the adjacent rib 212. The other end of the elbow 214 points laterally into the space below the downwardly concave backing wall 200 and sealingly and fixedly connects to the left (in FIG. 32) end of the flexible peristaltic pumping hose 202. Opposed slightly rearward converging steps 217 extend rearward adjacent the corresponding notches 213 in the lower left (FIGS. 32 and 34) corner of the body 191 where the hoses 203 and 202 fixedly and sealingly interconnect by sleeving over the grooved ends of the elbow 214. The convergent pairs of steps 217 each form an undercut into which the corresponding end portion of the corresponding hose 203 or 202 is forcibly and resiliently forwardly pressed at a point where the corresponding hose passes over an annularly grooved portion of the elbow 214, so as to frictionally and through an interference fit tend to prevent rearward escape of the elbow 214 and corresponding hose ends of the hoses 202 and 203 out of the body 191.

In the embodiment shown, a straight line fitting 215 fixedly and sealingly connects the hose portions 202 and 204 (here at the right side of the body 191 as seen from the rear in FIG. 32). A preferably integral, U-shaped undercut spring clip 216 extends rearward from the cassette front wall 195, as seen in FIGS. 32 and 34. The spring clip 216 grips snugly, in snap fit fashion, the soft deformable hose pumping portion 202 where it surrounds a grooved portion of the straight line fitting 215. The fitting 215 is thus fixedly held in place on the cassette body 190. The outflow hose 204 extends laterally from the cassette body 190 by means of another notch 213 rearward opening in the corresponding side 194 of the cassette body.

The cassette has laterally spaced legs laterally flanking the concave backing wall 200 (FIG. 34) and spaced on opposite sides thereof. The legs 220 are located between the ends 192 and 193 of the body 191 adjacent the central portion of the backing wall 200. The legs 220 extend rearward from the body sides 194. Feet 221 on the rear ends of the legs 220 extend laterally (here outwardly) therefrom for blocking forward displacement of the cassette away from the mounting plate 150 of the console as hereafter discussed.

The cassette further has a laterally spaced resilient leaf spring-like arms 222 extending rearward from the body 191 and angled laterally rearwardly and away from each other. The arms have rear tips 223 for blocking longitudinal displacement of the cassette 190 with respect to the console mounting plate 150. The laterally outer faces of the arms 222 are preferably textured as indicated at 224 (for example by means of grooves or ridges transverse to the length of the arms) to facilitate gripping between the thumb and a finger of the user for squeezing, and thereby bending, the arms 223 laterally toward each other to thereby bring the tips 223 laterally closer to each other. In the preferred embodiment shown, the arms 222 are molded integrally with the body 191 and connect therewith at the front face 195, the arms 222 extending rearward in an elongate, angled fashion so as to protrude and somewhat beyond the rear extent of the body. In the preferred embodiment shown, the body sides 194 are necked in laterally toward each other as indicated at 225 to form laterally outwardly concave recesses, such that the arms 222 are contained laterally in such recesses 225 and their tips 223 are, at rest, substantially closer together laterally than are the feet 221.

Figure 31:
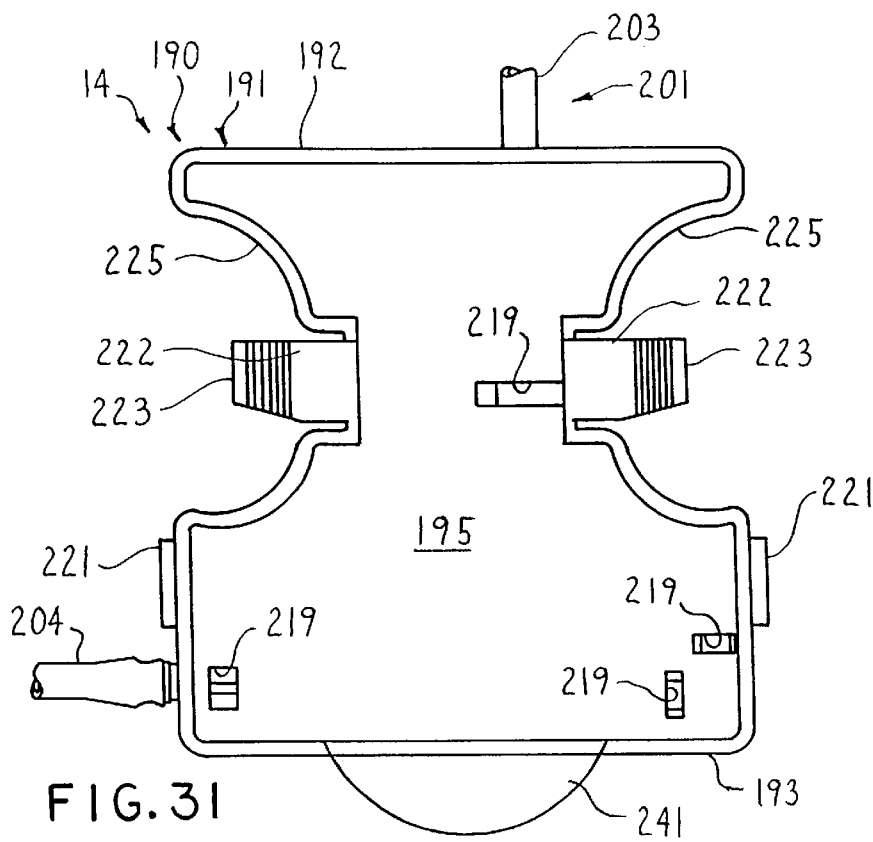
FIG. 31 is a front view of a pump cassette of the kind shown installed in pumping position on the FIG. 1 pump console.
Figure 33:
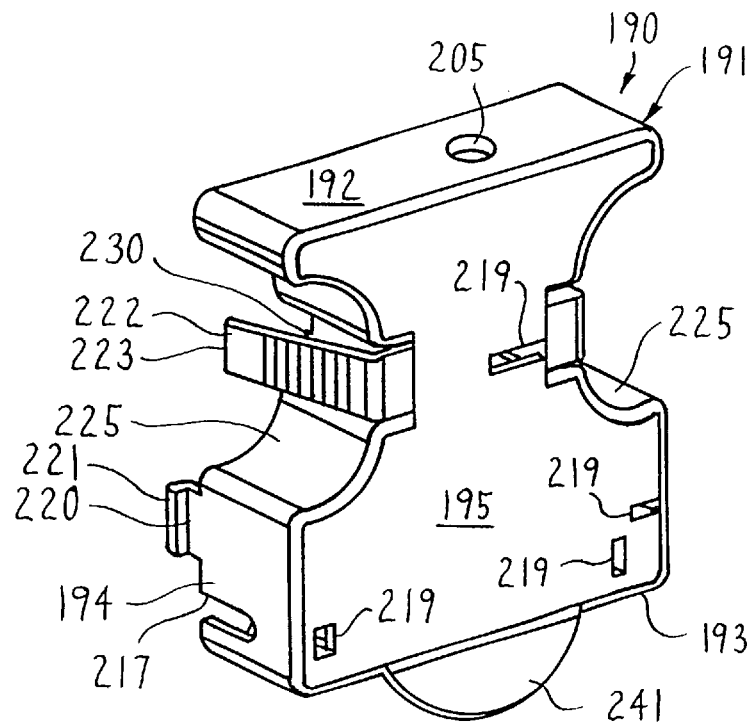
FIG. 33 is a pictorial view of the FIG. 31 cassette taken from the angle to show the top, left side and front thereof.

Holes 219 in the plate-like front wall 195 of the body 191 are located in front of the above described spring clip 216, rearward convergent step pairs and L-shaped keeper bar 218, as indicated in FIGS. 31 and 33, and are here left by special mold inserts (not shown) which are placed to form the spring clip 216, step pairs 217 and L-shaped keeper bar 218 during the molding of the cassette 190.

The cassette body 191 further includes a pair of parallel, longitudinally (vertically in FIG. 34) aligned, guide ridges 230 which extend rearward from the rear plane of the cassette body 191. In the preferred embodiment shown, the guide ridges 230 are rearward extensions of the sides 194 at the minimum separation of such sides in the recesses 225. The guide ridges 230 are thus, in the embodiment shown, flanked at least at their top portions by the arms 222, as seen in FIG. 32.

The concave backing wall 200 in its major central portion has a relieved and sloped rear edge 233, which is sloped to face rearward and downward (in FIG. 32) at an angle complementary to the sloped front face 175 of the arcuate cam 173 on the mounting plate 150 of the console. The sloped relieved rear edge 233 extends upward and rearward into ones of the reenforcing ribs 212 which converge toward and back the top of the concave backing wall 200. The relieved sloped portion of the rear edge 233 of the concave backing wall 200 extends almost the entire width thereof, in the embodiment shown ending at 234 at a sufficient lateral width to clear the lateral ends of the arcuate cam 173 on the mounting plate 150 of the console.

The central portion 240 (FIG. 32) of the cassette bottom 193 is open to clear the orbiting pump rollers 165. A convexly rounded portion 241 of the cassette plate-like front wall 195 extends down below the cassette bottom 193 to cover the orbit of the pump rollers 165 and to fit snugly in a front edge recess 242 (FIGS. 35 and 36) of the hollow 172 at the bottom of the mounting plate 150 of the console.

OPERATION

In the preferred embodiment shown, the tube set 14 and tool 12 are each prepackaged, disposable, single use, presterilized (by the manufacturer) devices, the handpiece 11 is sterilizable, and the handpiece and console 13 are reusable, multiple use devices.

Prior to use, the console 13 is located in the surgical operating room remote from the operating table (or other patient support) and is connected to a suitable electric power source EP (FIG. 1) at least for powering the peristaltic pump motor 152, as well as any other control functions that may be provided, e.g., as indicated by the dotted lines 22 and 23, control of the handpiece power source PO and suction source SU.

The tube set 14 is readied for use (typically by removal from a sterile package). The cassette 190 can then be installed on the mounting plate 150 of the console 13. To that end, the cassette 190 is moved forward into contact with the front of the mounting plate 150 with the cassette feet 221 entering the mouths 181 of the mounting plate slots 180. In this position, the rear of the cassette body 191 abuts the front face of the mounting plate 150, the tips 223 of the cassette arms 222 lie in the upper portions of the mounting plate recesses 182 above the wedge shaped portions 183, the cassette guide ridges 230 lie in the upper portions of the mounting plate guide grooves 186 and the cassette concave backing wall sloped rear edge 233 is spaced above the mounting plate arcuate cam 173.

The user then completes installation of the cassette 190 on the mounting plate 150 by simply moving the cassette downward on the mounting plate into its operative position shown in FIGS. 36–38.

Thus, the cassette legs 220 move downward in the mounting plate slots 180 below the mouths 181 thereof with the feet 221 trapped behind the mounting plate. The sloped front face 175 of the mounting plate arcuate cam 173 cams the hose pumping portion 202 forward onto the center of the rollers 165 (FIG. 37), thus insuring the pumping hose portion 202 does not get caught between the rollers 165 and the mounting plate 150.

Also during such downward cassette movement, the tips 223 of the arms 222 of the cassette ride the ramps 184 downward and inward, and finally spring laterally outwardly apart to lodge snugly under the mounting plate steps 185 to thereby lock the cassette 190 against unintended upward movement along the mounting plate 150.

The downward movement of the cassette 190 on the mounting plate 150 is in part guided by movement of the cassette guide ridges 230 downward in the mounting plate guide grooves 186 to a lower position therein.

With the cassette 190 thus installed on the mounting plate 150, in its operative position shown in FIGS. 1 and 36–38, the orbit of the pump rollers 165 is covered in front by the plate-like front wall 195 and convex rounded portion 241 thereof, of the cassette body 191, with the bottom edge of the convexly rounded portion 241 snugly received in the front edge recess 242 of the mounting plate hollow 172. Also in this installed position, the cassette concave backing wall 200 is flush with and extends forward from the downward facing arcuate cam concave face 174 of the backing plate 150 to provide an essentially continuous downwardly concave surface overlying the pump rotor 160 as generally indicated in FIGS. 36 and 37. This enables the pump rollers 165 to compress the hose pumping portion 202 against the cassette concave backing wall 200 as indicated in FIG. 37.

To ready same for use, the handpiece 11 is connected through the cable 21 to the power and suction sources PO and SU respectively, as seen in FIG. 1. A tool 12 may then be chucked in the handpiece 11 and the irrigation outflow hose 204 from the cassette 190 may then be connected, as indicated at 73, to the irrigation liquid inflow fitting of the tool 12. If desired, the outflow hose portion 204 may be secured to the body of the handpiece 11 by any convenient releasable clip means, not shown. The irrigation liquid inflow hose portion 203 may then be plugged on at 210 into a conventional irrigation liquid supply bag IB.

In surgical use, the peristaltic pump, defined by the cassette 190 and pump rotor 160 can be operated to supply irrigation liquid to the tool 12 and therethrough to the surgical site SS (FIG. 1). The peristaltic pump can be operated continuously by continuous energization of its motor 152 or discontinuously by turning on and off its motor 152. Turning on and off of the peristaltic pump motor may be accomplished by means near the surgical site such as a user operated foot switch or the like or by suitable switching on the console 13 in a conventional manner. If desired, means (not shown) may be provided on the outflow hose 204 to close or open flow therethrough and such means may be provided close to or on the handpiece for convenient use.

In use, the tool inner rotor 40 is rotated by the powered rotation source 15 of the handpiece 11, while the tool housing 30 is fixed with respect to the handpiece outer casing held by the surgeon. The rotating inner tube 42 thus rotates its inner window 47 repetitively passed the outer window 46 (FIGS. 2–4) of the outer tube 32 to accomplish a shearing type tissue cutting action. Tissue working can be accomplished with a variety of window configurations at 46, 47, including that shown in FIG. 4. For example, a more aggressive tissue cutting action can be accomplished by substituting the modified outer tube window configuration at 46A of FIGS. 29 and 30, with its teeth 142 in rotating cutting cooperation with the teeth 133 on the inner tube window 47.

As above discussed with respect to FIGS. 2 and 3, irrigation flow may be combined with suction flow (FIG. 2) or used alone to provide irrigation liquid to the surgical site.

As to the latter, and as schematically shown in FIG. 3, irrigation liquid flow through the fitting 73 and the annular flow space between the inner and outer tubes and thence through the port 131 provides irrigation liquid to the inside of the inner tube near its front end and thereby allows outflow of such irrigation liquid to the surgical site SS, through the windows 46 and 47 as they periodically mesh. On the other hand, when it is desired to remove debris from the surgical site, e.g. after cutting, provision of suction rearward through the inner tube 42 (as schematically indicated by arrows in FIG. 2) draws at least some of the irrigation liquid flowing into the inner tube through the hole 131 rearwardly along the inner tube to entrain and thereby retrieve unwanted debris from the surgical site SS. The irrigation flow path between the inner and outer tubes has been described in detail above with respect to FIG. 5A, for example, and need not be repeated, as has the assembly of the tool 12 and its installation and removal from, the handpiece 11.

While the tool 12 disclosed above in connection with FIGS. 1–30 is successful in outer tube 32 diameters exceeding 3.0 millimeters and thus is adapted for relatively large scale surgical sites, such as in endoscopic knee surgery, certain surgical procedures, in particular pediatric ear, nose and throat (ENT) surgery requires tools, particularly cutters, of outer tube outside diameter less than 2.7 millimeter and more typically 2.5 millimeter or less. Attempts to scale down the FIGS. 1–30 cutter to 2.7 millimeter or less outer tube outside diameter, or for that matter other cutter designs in which irrigation flow is through an annular passage between the inner and outer tubes, have proved unsuccessful. This is due to inability to provide sufficient irrigation liquid flow, sufficient tube resistance to bending, and/or sufficient, reliable, clog resistent suction of tissue bits from the surgical site through the inner tube.

Accordingly, FIGS. 39–42 show a modified tool 12E. Embedding aspects of present invention and instructed by way of example is a cutter. In the following discussion of FIGS. 39–42 of tool 12E, the structure is similar to that disclosed above with respect to the tool 12 of FIGS. 1–30 will carry the same reference numerals thereas, with the suffix "E" added. The tool 12E is generally similar to the tool 12 except as follows.

Tool 12E includes hubs 31E and 41E which are similar in external size and configuration to the hubs 31 and 41, so as to be used with the same handpiece. However, the inner diameter of the hubs 31E and 41E is less than that of the hubs 41 and 31, to respectively fit and fixed to the outer periphery of the outer diameter outer tube 32E and of a modified inner tube 300.

The tool 12E of this embodiment is especially suitable for ear-nose-and-throat procedures, and may also be used for other similarly sealed micro surgical applications.

By way of example, in one particular unit constructed in accord with this embodiment, the outer tube outside diameter was 2.5 mm and more particularly about 0.094 inch. The inner diameter of the outer tube was about 0.077 inch. The inner tube outside diameter was 0.072 inch and its inner diameter was about 0.055 inch. Maintaining the inner tube inner diameter at about 0.055 inch is necessary to provide adequate suction of tissue bits from the surgical site. Thus in this particular unit, the inner tube and outer tube wall thicknesses are about 0.008 to 0.009 inch, leaving only about a 0.002 to 0.003 inch annular gap therebetween.

The Applicants Assignee has found by experimentation that the small annular gap does not provide adequate irrigation liquid flow from the inlet nipple 73E to the windows 347 and 46E. It has been found that reducing the outer diameter of the inner tube 300 enough to provide an annular gap radially wide enough to provide adequate irrigation liquid flow from the nipple 73E to the windows 347 and 46E requires either a substantial reduction in inner tube wall thickness or a substantial reduction in inner tube inside diameter. The former design fabrication of the inner tube 300 results in an impermissible structural weakening of the innertube. The latter design fabrication of the inner tube 300 results in a reduced-diameter flow channel 302 through which the suction can be drawn. The reduction in the size of channel 302 increases the likelihood that cut tissue and other matter will clog the channel.

However, this problem is overcome in the current invention by forming in the outer periphery of the inner tube 300 an axially elongate cordial flat 260 which extends from a location slightly to the rear of the opening out of irrigation inlet 74E to the window 347 formed in the distal end of the tube. This flat 260 establishes a usable irrigation flow path from the nipple 73E to the window 347 and thus indeed to the outer tube window 46E. In the depicted version of the invention, flat 260 subtends an arcuate section of the outer surface of inner tube 300 of approximately 60°.

Figure 42:
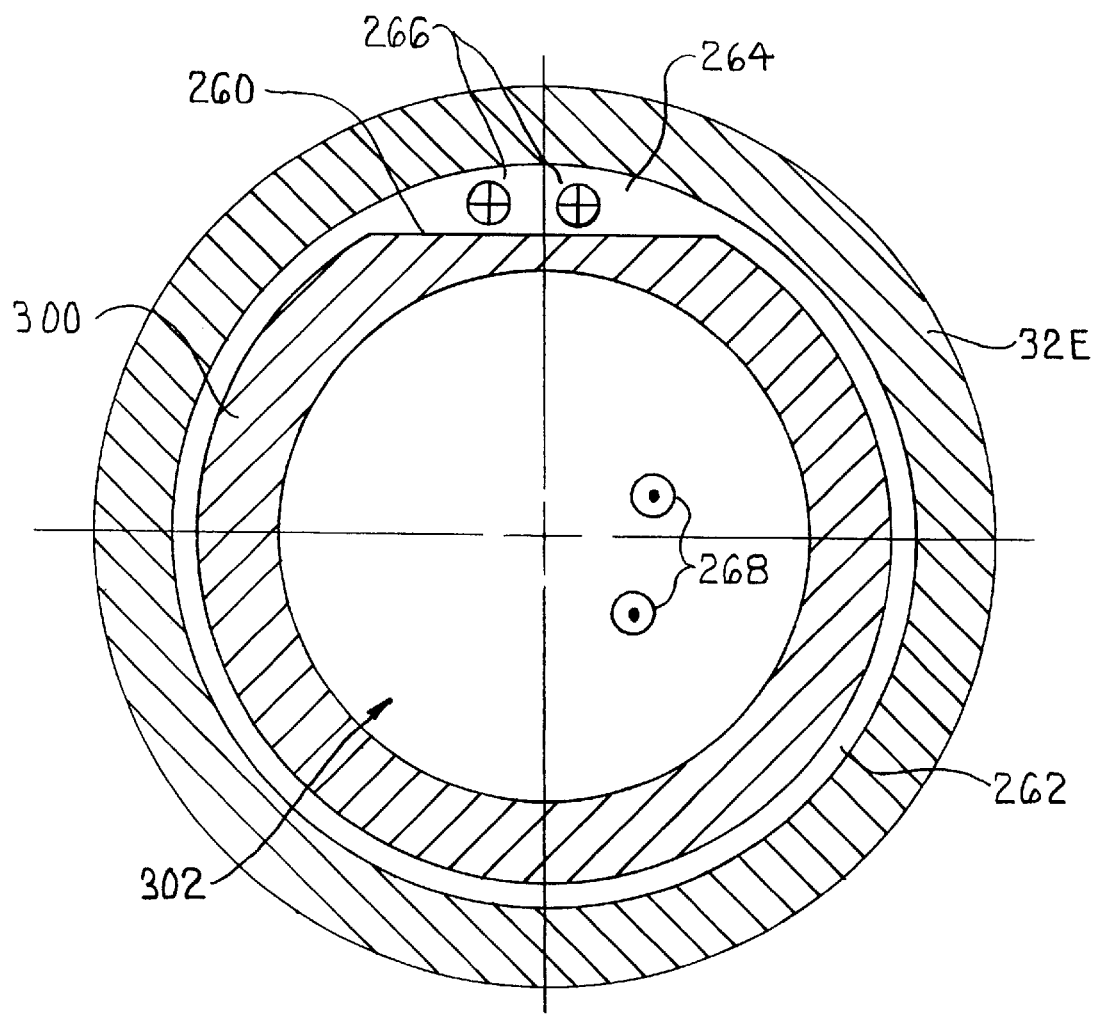
FIG. 42 is a cross sectional view through the inner and outer tubes of the FIG. 39 cutter taken along line 42—42 of FIG. 40 wherein the fluid flow paths through the cutter are depicted.

Accordingly, as seen in FIG. 42, in the assembled tool 12E, the inner surface of outer tube 32E and the outer surface of inner tube 300 collectively define a radially narrow C-shaped gap 262 extending from one end of the chordal flat 260 to the other. Owing to the narrow radial width of gap 262, only small volumes of irrigation fluid can flow from passage 74E toward windows 46E and 347. However, inner tube chordal flat 260 and the opposed inner surface of the outer tube 32E define a radially wide D-shaped channel 264 from passage 74E to window 347. Irrigation fluid easily flows in sufficient quantity through this channel 264 from the nipple 73E to the windows 46E and 347. The channel 264 has a radial width, a depth, several times (about 3 times in FIG. 42) greater than the radial width of the gap 262. For example, in the above-discussed unit in which the gap 262 had a radial width of about 0.002 to 0.003 inches, the channel 264 had a maximum radial width (the largest distance between flat 260 and the adjacent inner wall of the outer tube 32E) of approximately 0.006 to 0.008 inches.

Despite the reduction of wall thickness of the inner tube at the cordial flat 260, the rigidity (resistance to bending) of the inner tube 300 is not significantly compromised. This is believed due to the fact that at least approximately half the average wall thickness of the inner tube remains even at the circumferential center of the cordial flat 260. Also the wall thickness increases rapidly towards the circumferential edges of the flat 260. Further, the circumferential narrowness of the flat 260 leaves the great majority of the inner tube 300 circumference at full wall thickness. Thus, just as a tube with its circumference broken by a radial through slot still retains substantial resistance to bending, given an adequate wall thickness to diameter ratio, even more so the circumferentially complete inner tube 300 maintains adequate resistance to bending despite the presence of the cordial flat 260 which at most reduces the inner tube wall thickness at one circumferential point to about half. In any event, the inner tube would be weakened substantially more if reduced in outside diameter to provide a sufficiently radially thick annular irrigation liquid flow passage, instead of the D-shaped passage 264 defined by the flat 260.

In addition, the flat 260 can be provided by relatively simple and inexpensive machining procedure even in a tool 12E slim enough for pediatric ENT surgery.

Accordingly, it is anticipated that, in some versions of the invention, the outer diameter of outer tube 32E will be less than 0.16 inches and, in other versions of the invention, the outer diameter of the outer tube will 0.114 inches or smaller. In still other versions of the invention, the outer diameter of the outer tube will be 0.098 inches or less. In these versions of the invention, it is anticipated that the inner diameter of the outer tube 32E will 0.13 inches or less and, in other versions of the invention, 0.095 inches or less. In still other versions the inner diameter of the outer tube 32E will be 0.080 inches or less. In these versions of the invention, it is anticipated that the outer diameter of the inner tube 300 will be 0.115 inches or less and, in other versions of the invention, 0.085 inches or less. In other versions of the invention, the outer diameter of the inner tube will be 0.075 inches or less. Generally, in these versions of the invention the thickness of the wall defining the inner tube 300 will be less than 0.012 inches; in other versions of the invention, this thickness will be 0.010 inches or less. Owing to the spacing between the outer tube 32E and inner tube 300, gap 262 has a width of less than 0.008 inches or less and usually 0.005 inches or less. In still other versions of the invention, this width may be 0.003 inches or less.

Figure 40:
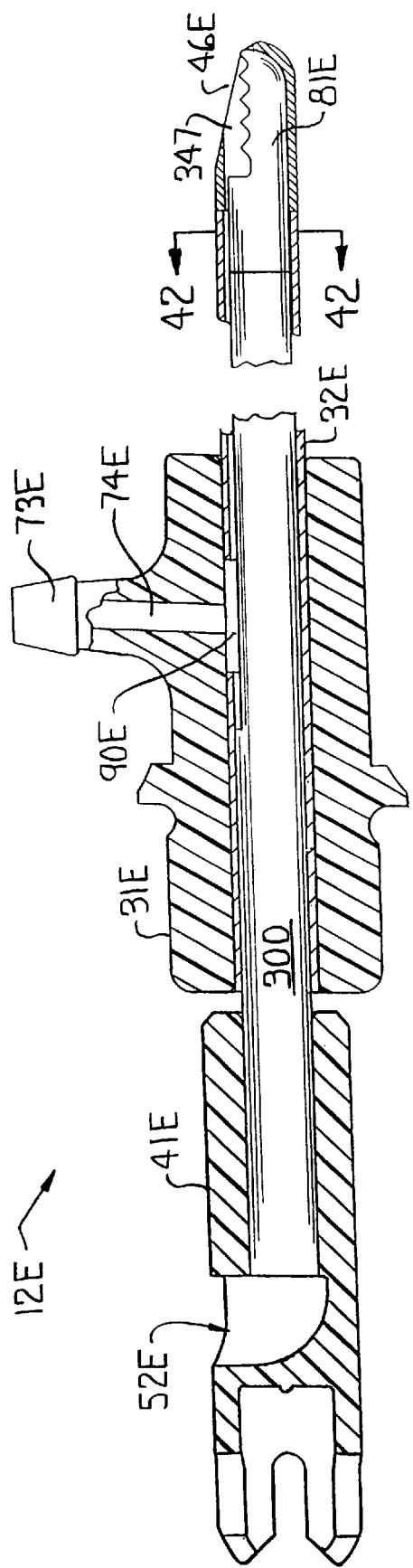
FIG. 40 is an enlarged, fragmentary central cross sectional view of the FIG. 39 cutter.

Thus, as represented by FIG. 40, when the tool 12E of this embodiment of the invention is actuated and supplied with irrigation fluid, as the inner tube 300 rotates, channel 264 periodically comes into registration with the opening of passage 74E and opening 90E of outer tube 32E. Consequently, the fluid is introduced into the channel 264 and flows downstream towards the window 347 as represented by arrow tails 266 in FIG. 42. Owing to the suction drawn on rotor 41E, this fluid, and any debris entrained therein, are drawn out through the center channel 302 of the inner tube 300 as represented by arrow heads 268.

Thus, tool 12E of this embodiment of the invention is sufficiently small in size so that it can be used to perform micro surgical procedures, such as pediatric ENT surgical procedures. The tool 12E is further configured so that fluid can be introduced into the tool and delivered to windows 46E and 347 at the distal end of the tool 12E. This fluid serves as a medium in which debris generated at the surgical site is entrained and drawn from the surgical site. Thus, the tool of this invention is a single assembly that can be used to perform a pediatric ENT or other micro cutting procedure, introduce fluid to the surgical site at which the procedure is performed and draw a suction from the surgical site.

Still another feature of tool 12E is that tubes 32E and 300 are collectively shaped so that proximal end of window 46E is spaced forward of the proximal end of window 347. Thus, as seen in FIG. 40, window 347 extends rearwardly, towards hubs 31E and 41E, beyond the proximal, rear, end of window 46E.

In the event abuse or activity causes material to become stuck in the windows 46E and 347, continued rotation of the inner tube 300 may result in the structural failure of the inner tube nose piece 81E. This failure will most likely result in the portion of the nose piece 81E forward from the proximal end of window 347 separating from the rest of inner tube 300. Since the outer tube 32E extends over and forward from the proximal end of the inner tube window 347, loose portions of the nose piece 81E formed by the separation should stay trapped within the outer tube 32E. Thus, the relative shaping of the tube windows 32E and 347 prevents loose fragments that separate from the inner tube from coming out of the tool 12E and entering the surgical site.

It should be realized that the foregoing discussion has been limited to a preferred version of the invention and that other versions (some perhaps less preferred) of the invention may vary from what has been described. For example, in the disclosed version of tool 12E, the tool is described as a cutter. In other versions of the invention, the tool may be illustrated as a burr. In these versions of the invention, the outer tube 32E would most likely be formed with a much wider window than described. A burr head is secured to the distal, most forward end of the inner tube 300. In these versions of the invention, owing to the narrow separation between the inner surface of the outer tube 32E and the outer surface of the inner tube 300, the inner tube will be shaped to have the channel-defining flat 260 extend along the length of the inner tube.

Also, in not all versions of the invention may it be necessary that the channel-defining flat 260 extend rearwardly from the associated window 347 of the inner tube 300. In some versions of the invention, flat 260 may, relative to the longitudinal axis of inner tube 300, be angular offset from window 347. For example, the flat 260 may be diametrically opposed to the longitudinal center of window 347 relative to the longitudinal axis of the inner tube 300. In these versions of the invention the flat 260 may terminate at a port similar to port 131 described with respect to tool 12 (FIG. 3). Also, in still other versions of the invention, the inner tube 42a may be provided with plural spaced apart flats 260 that define plural channels through which the irrigation fluid can flow.

Moreover, the arcuate section of the outer surface of the inner tube 42 subtended by the flat, or plural flats, may vary from what has been described. Also, there is no requirement that, in each version of the invention, the flats 260 extend axially linearly along the length of the inner tube 300. In some versions of the invention, the flats may extend helically along the outside of the inner tube 300 for either the partial or complete length of the tube.

Moreover, in preferred versions of the invention, inner tube 300 is formed so that 40 to 60% of the original wall of the tube remains in place along the thinnest section of the tube after flat 290 is formed. However, in some versions of the invention, the amount of material removed from the outer surface of inner tube 300 to form flat 290 may be such that the thinnest section of the tube has a wall thickness of between 10 to 90% of the original wall thickness of the tube. Also, flat 290 may be formed by means other than the removal of material from tube 300. In some versions of the invention, for example tube 300 may be formed by an extrusion process. In this process the flat 290 is formed as part of the process of extruding the tube 300.

Therefor, it is an object of the appended claims to cover all such variations and modifications that come within the true spirit and scope of this invention.

What is claimed is:

1. An elongate irrigated surgical tool engagable with and powerable by a powered surgical handpiece having a rotatable drive member, said tool comprising:

a tubular housing comprising a first hub fixable to the handpiece and an elongate outer tube extending forward from said first hub, said outer tube having a first window engagable with a surgical site and an inner surface; and a tubular rotor comprising a second hub engagable with and rotatable by the drive member of the handpiece, said second hub being located adjacent a rear end of said first hub, and an inner tube attached to said second hub that is disposed in and rotatable relative to said first hub and said outer tube, said inner tube having: an outer surface that has an outer diameter, the outer surface of the inner tube and the inner surface of said outer tube defining an a circular gap having a select width between said inner tube and said outer tube; a front portion including a tissue working portion engagable through the first window of said outer tube with tissue at the surgical site; a central passage, the central passage having a rear portion connectable to a suction source; and an inner diameter extending from the front portion to the rear portion, the inner diameter having sufficient size so that fluid can be drawn from the surgical site to the rear portion, wherein:

said tubular housing has a member connectable to a source for supplying an irrigation fluid, said member having a passage opening directed to the outer surface of said inner tube through which the irrigation fluid flows; and said inner tube and said outer tube are further formed to define between said tubes at least one channel having a depth greater than the width of the circular gap between said tubes that extends from said member passage opening of said tubular member towards the front portion of said inner tube through which the irrigation fluid flows from said member passage opening.

2. The surgical tool of claim 1, wherein said outer tube has an outer diameter less than 0.16 inches and the circular gap between said tubes is less than 0.008 inches.

3. The surgical tool of claim 1, wherein said inner tube is formed to have an elongated flat surface that extends longitudinally along an outer surface of said inner tube from the front portion to a position along said inner tube that is subtended by the member passage opening of said tubular housing, wherein said flat and the inner surface of said outer tube collectively define the at least one channel extending between said inner tube and said outer tube.

4. The surgical tool of claim 3, wherein said outer tube has a maximum outer diameter of 0.114 inches and the circular gap between said tubes has a width of 0.005 inches or less.

5. The surgical tool of claim 3, wherein: said first hub is formed with said member connectable to the source of irrigation fluid and the member passage opening is located in said first hub; and the flat extends along the outer surface of said inner tube to a location at which the flat will subtend the member passage opening in said first hub.

6. The surgical tool of claim 1, wherein said inner tube front portion is provided with a closed front end tip and said front end tip is provided with a second window that forms said tissue working portion.

7. The surgical tool of claim 6, wherein said inner tube and said outer tube are formed so that the channel extends linearly along said inner tube from said second window towards a section of said inner tube subtended by the member passage opening in said tubular housing.

8. The surgical tool of claim 6, wherein the outer surface of said inner tube has a generally circular cross sectional profile and is formed with a flat face that intersects the circular portion of the outer surface of said inner tube and the flat face extends linearly, longitudinally along the outer surface of said inner tube from said second window to a section of said inner tube subtended by the passage opening in said tabular housing member.

9. The surgical tool of claim 1, wherein: said member connectable to the source of irrigation fluid extends from said first hub and the passage opening of said member is open towards said inner tube; and said at least one channel extends from said first hub.

10. A surgical tool for use with a powered surgical handpiece, said surgical tool including:
- an inner hub adapted for connection to and rotation with a rotating drive member of the surgical handpiece, said inner hub having an outlet port through which a suction is drawn;
- a hollow inner tube secured to said inner hub so as to rotate in unison with said inner hub, said inner tube having an exposed rear section located adjacent said inner hub and a front section spaced distal from said inner hub, said front section of said inner tube being provided with a tissue working member and being formed with a window into which fluid can flow into said inner tube and to the outlet port of said inner hub, said inner tube being formed to have an outer surface with a generally circular cross section and at least one flat surface that extends along said inner tube from said front section to said rear section;
- an outer hub disposed over said rear section of said inner tube, said outer hub being releasably securable to the handpiece and being formed with a passage through which irrigation fluid is introduced towards the inner tube, said passage having an opening that is periodically subtended by the flat formed on the outer surface of said inner tube when said inner tube is rotated; and
- an outer tube integrally attached to said outer hub, said outer tube extending over said inner tube and having a window adjacent said tissue working member of said inner tube through which said tissue working member is exposed to a surgical site and an inner wall, the inner wall of said outer tube and said at least one flat of said inner tube collectively defining at least one channel through which irrigation fluid flows from the passage opening of said outer hub to the window of said outer tube.

11. The surgical tool of claim 10, wherein said inner tube and said outer tube are collectively shaped to define a curved gap between said tubes, said curved gap having a width and the channel formed by the flat of said inner tube and said outer tube intersects the curved gap and has a depth that is greater than the width of the curved gap.

12. The surgical tool of claim 11, wherein said outer tube has a maximum outer diameter of 0.114 inches and the curved gap between said inner tube and said outer tube has a width of 0.005 inches or less.

13. The surgical tool of claim 10, wherein said outer tube has a front end with a nose piece that extends over the tissue working member of said inner tube and said nose piece is formed with the window of said outer tube.

14. The surgical tool of claim 13, wherein said inner tube front portion is provided with a closed tip and the window of said inner tube is formed in said closed tip and the window of said inner tube forms the tissue working member.

15. The surgical tool of claim 10, wherein said inner tube front portion is provided with a closed tip and the window of said inner tube is formed in said closed tip and the window of said inner tube forms the tissue working member.

16. A surgical tool for use with a powered surgical handpiece having a rotating drive member, said surgical tool comprising:
- an outer hub adapted to be releasably secured to the handpiece, said outer hub having a rear end, a front end, a hollow center open towards the front end and a member configured to receive a conduit through which irrigation fluid is flowed, said member having a passage opening that opens into the center opening of said hub;
- a hollow outer tube rigidly secured to said outer hub that extends forward from said outer hub, said outer tube having a rear end that is open towards the hollow center of said outer hub, an inner wall with a circular profile and a closed front end that is spaced from the rear end, the front end being formed to define a window that extends through said outer tube;
- an inner hub located adjacent the rear end of said outer hub that is configured to engage and rotate in unison with the rotating drive member of the handpiece and a bore through which a suction is drawn, the bore being open towards a front end of said inner hub; and
- a hollow inner tube that is integrally attached to said inner hub, said inner tube extending forward from the bore of said inner hub and extending through the center of said outer hub and being seated inside said outer tube, said inner tube having a closed front end located within the front end of said outer tube and a window formed in the inner tube front end, the windows of said outer and inner tubes being collectively shaped to form a tissue cutting assembly, wherein said inner tube is shaped to have an outer wall with a generally curved cross section profile and a flat section that extends along said outer wall from the window of said inner tube to a position subtended by the passage opening formed in said outer hub.

17. The surgical tool of claim 16, wherein said outer tube has an outer diameter less than 0.16 inches.

18. The surgical tool of claim 16, wherein said outer tube and said inner tube are shaped so that there is an annular gap between the inner wall of said outer tube and the outer wall of said inner tube, said flat defines a channel that intersects the annular gap, the annular gap has a width of 0.008 inches or less and the channel has a depth greater than the width of the annular gap.

19. The surgical tool of claim 16, wherein said outer tube has an outer diameter less than 0.114 inches.

20. The surgical tool of claim 19, wherein: the inner wall of said outer tube has a diameter; said front end of said outer tube is formed by a tip having an inner diameter; and the inner diameter of said tip of said outer tube is less than the diameter of the inner wall of said outer tube.

21. The surgical tool of claim 16, wherein said inner tube has a wall thickness and is formed to have a thinnest wall thickness at the flat section wherein the thinnest thickness of the flat section is between 10 and 90% of the wall thickness of the curved section of said tube.

22. The surgical tool of claim 16, wherein said inner tube has a wall thickness and is formed to have a thinnest wall thickness at the flat section wherein the thinnest thickness of the flat section is between 40 and 60% of the wall thickness of the curved section of said tube.

23. An elongate irrigated surgical tool engagable with and powerable by a powered surgical handpiece of the kind having a casing and a rotatable drive member, said tool comprising:

a tubular, outer housing including a mounting hub for fixed mounting on the surgical handpiece casing and a forward extending outer tube, said outer tube having a closed front portion that is shaped to define a first window; and a tubular, inner rotor including a rotor hub rotatably drivable by a powered surgical handpiece rotatable drive member for rotatably driving said rotor, and an inner tube fixedly projecting forward from and rotatable with said rotor hub, said rotor hub and said inner tube having communicating coaxial bores defining a common inner fluid passage, said inner tube being disposed in said outer tube and having a closed front portion that is shaped to define a second window and a port that is spaced apart from said second window and said rotor hub having a suction connection connectable to a suction outlet source through which fluid is drawn from the inner fluid passage, wherein:

said first window of said outer tube and said second window of said inner tube are positioned to be aligned with each other and at least one of said windows has an edge for working patient tissue upon rotation of said inner tube within said outer tube, said windows communicating with the inner fluid passage of said inner tube, the inner fluid passage extending at least to said windows;

said outer tube and said inner tube define an irrigation liquid flow passage disposed radially between said inner and outer tubes that extends from adjacent said mounting hub toward said inner tube front portion;

said inner tube front portion is in snug rotative bearing contact with said outer tube front portion and therewith forming a rotate bearing for rotatably supporting said inner tube in said outer tube, said inner tube having an elongate intermediate portion extending rearward from the front portion of said inner tube and being radially spaced from said outer tube to define at least an intermediate portion of said irrigation liquid flow passage; and said inner tube front portion defines an axially elongate liquid channel in an outer periphery thereof at said rotate bearing that extends rearwardly from the port formed in said inner tube for extending said irrigation liquid flow passage forward to said port.

24. The tool of claim 23, wherein said channel is defined by a chordal flat that extends axially along said outer periphery of said inner tube from said port formed in the forward portion of said inner tube and extends rearward toward said elongate intermediate portion of said inner tube.

* * * * *

UNITED STATES PATENT AND TRADEMARK OFFICE
CERTIFICATE OF CORRECTION

PATENT NO.     : 6,342,061 B1
DATED          : January 29, 2002
INVENTOR(S)    : Barry J. Kauker et al.

It is certified that error appears in the above-identified patent and that said Letters Patent is hereby corrected as shown below:

Column 18,
Line 40, change "tubular member" to -- tubular housing --
Line 52, change "flat and" to -- flat surface and --
Line 61, change "the flat extends" to -- the flat surface extends --
Line 62, change "flat will" to -- flat surface will --

Column 19,
Line 13, change "tabular housing" to -- tubular housing --
Line 35, change "extends along" to -- extends longitudinally along --
Line 41, change "that is periodically subtended" to -- that is positioned so the opening is periodically subtended --

Column 20,
Line 17, change "the center opening of" to -- the center of --
Line 20, change "the hollow center" to -- the center --
Line 40, change "extends along" to -- extends longitudinally along --
Line 66, change "have a thinnest" to -- have thinnest --

Column 21,
Line 23, change "suction outlet source" to -- suction source --

Column 22,
Line 25, change "a chordal flat" to -- a first chordal flat --
Line 27, change "tube and extends" to -- tube which extends --

Signed and Sealed this

Twenty-fifth Day of February, 2003

JAMES E. ROGAN
*Director of the United States Patent and Trademark Office*